US011653452B1

(12) United States Patent
Sundberg et al.

(10) Patent No.: US 11,653,452 B1
(45) Date of Patent: May 16, 2023

(54) FLEXIBLE CIRCUIT BOARD DESIGN IN A BRAIN COMPUTER INTERFACE MODULE

(71) Applicant: Meta Platforms, Inc., Menlo Park, CA (US)

(72) Inventors: John Michael Sundberg, Concord, CA (US); Alvin Alza Dominguez, San Jose, CA (US)

(73) Assignee: Meta Platforms, Inc., Menlo Park, CA (US)

( * ) Notice: Subject to any disclaimer, the term of this patent is extended or adjusted under 35 U.S.C. 154(b) by 291 days.

(21) Appl. No.: 17/000,216

(22) Filed: Aug. 21, 2020

Related U.S. Application Data

(60) Provisional application No. 63/009,358, filed on Apr. 13, 2020.

(51) Int. Cl.
| | | |
|---|---|---|
| *A61N 1/04* | (2006.01) | |
| *H05K 1/18* | (2006.01) | |
| *H05K 1/11* | (2006.01) | |
| *A61N 1/05* | (2006.01) | |
| *A61B 5/291* | (2021.01) | |

(52) U.S. Cl.
CPC .............. *H05K 1/189* (2013.01); *A61N 1/048* (2013.01); *A61N 1/0476* (2013.01); *H05K 1/118* (2013.01); *A61B 5/291* (2021.01); *A61N 1/0529* (2013.01)

(58) Field of Classification Search
CPC ...... H05K 1/189; H05K 1/118; A61N 1/0476; A61N 1/048; A61N 1/0529; A61B 5/291
See application file for complete search history.

(56) References Cited

U.S. PATENT DOCUMENTS

| 6,659,659 | B1 | 12/2003 | Malone | |
|---|---|---|---|---|
| 2003/0225323 | A1* | 12/2003 | Kiani | A61B 5/14552 |
| | | | | 600/323 |
| 2004/0136658 | A1 | 7/2004 | Kropp | |
| 2005/0062056 | A1 | 3/2005 | Baugh et al. | |
| 2006/0022213 | A1 | 2/2006 | Posamentier | |
| 2006/0162104 | A1 | 7/2006 | Malone et al. | |

(Continued)

OTHER PUBLICATIONS

United States Office Action, U.S. Appl. No. 17/000,212, filed May 18, 2021, 11 pages.

(Continued)

*Primary Examiner* — Ankit D Tejani
*Assistant Examiner* — Joshua Brendon Solomon
(74) *Attorney, Agent, or Firm* — Fenwick & West LLP

(57) ABSTRACT

A flexible printed circuit board (FPCA) of a brain computer interface (BCI) module is configured to interconnect a plurality of emitter assemblies and a plurality of detector assemblies of the BCI module. The FPCA comprises a connector portion for connecting the FPCA to a controller of the BCI module, a plurality of rigid sections, a plurality of flexible sections. A first subset of rigid sections is configured to mount the plurality of emitter assemblies. A second subset of rigid sections is configured to mount the plurality of detector assemblies. Each flexible section is configured to attach the two or more rigid sections of the plurality of rigid sections to each other. The plurality of flexible sections allows the plurality of emitter assemblies and the plurality of detector assemblies to stretch to conform to a head of a user.

14 Claims, 28 Drawing Sheets

(56) References Cited

U.S. PATENT DOCUMENTS

| | | |
|---|---|---|
| 2006/0189860 A1* | 8/2006 | Hacker .............. A61B 5/14553 |
| | | 600/323 |
| 2009/0088649 A1 | 4/2009 | Ninomiya et al. |
| 2009/0247839 A1 | 10/2009 | Ninomiya et al. |
| 2010/0317939 A1* | 12/2010 | Kuhn ................ A61B 5/14552 |
| | | 600/323 |
| 2011/0182570 A1 | 7/2011 | Yeh |
| 2016/0296810 A1 | 10/2016 | Mandel et al. |
| 2018/0294891 A1 | 10/2018 | Gudeman |
| 2020/0174207 A1 | 6/2020 | Cabessa et al. |
| 2021/0331160 A1 | 10/2021 | Cooper et al. |

OTHER PUBLICATIONS

Non-Final Office Action dated Mar. 16, 2022 for U.S. Appl. No. 17/000,217, filed Aug. 21, 2020, 13 pages.
Non-Final Office Action dated Nov. 8, 2022 for U.S. Appl. No. 17/000,214, filed Aug. 21, 2020, 15 pages.

* cited by examiner

Pattern Option 2:
S = Combined Red and Infrared source
D = Detector

Pattern Option 1:
I = Infrared source
R = Red Source
D = Detector

FLEXIBLE CIRCUIT BOARD DESIGN IN A BRAIN COMPUTER INTERFACE MODULE

CROSS REFERENCE TO RELATED APPLICATION

This application claims the benefit of U.S. Provisional Application No. 63/009,358, filed on Apr. 13, 2020, which is incorporated by reference in its entirety.

BACKGROUND

This disclosure relates generally to brain computer interface systems, and specifically to a wearable brain computer interface system with an increased dynamic range sensor.

Communication via physical actions, such as textual entry or manipulation of a user interface on a mobile or other device is a key form of interaction amongst individuals today. Additionally, certain online systems, such as online social networks, thrive on the network of users that frequent the online social network on a consistent basis. One component of online social networks is the ability of a user to interact with objects (e.g., electronically provided content) in an online or virtual setting. In many scenarios, detection of interactions requires the user to type or enter words and phrases through a physical means (e.g., a keyboard or clicking on a virtual keyboard) and/or to audibly provide commands. Physically entering words and phrases or providing audible commands may be cumbersome or impossible for certain individuals. Additionally, and more generally, physical entry of words and phrases for all individuals is often an inefficient way to communicate, as typing or otherwise manipulating various user interfaces can be cumbersome.

Brain computer interface (BCI) systems are being explored in relation to some of these problems. However, traditional brain computer interface (BCI) systems typically implement electrical signal detection methods to characterize brain activity. Such systems are typically used in clinical or academic settings, and often are not designed for use by users during their normal daily lives. In relation to user factors, such systems often lack features that allow users to properly position sensing components in a repeatable and reliable manner, as well as to maintain contacts between sensing components and desired body regions as a user moves throughout his or her daily life. Miniaturization of such BCI systems also provides challenges.

Other types of BCI systems use optical signals to characterize brain activity. Conventional optical wearable and non-wearable BCI systems implement fiber optics to couple light from the scalp to detectors and emitters. However, such systems are often bulky and inhibit a user's ability to perform other daily tasks. Accordingly, there exists a need for a compact BCI system that can be easily worn by a user.

Additionally, fields exploring other sensing regimes for detection and decoding of brain activity are nascent, and traditional sensors used for other sensing regimes have insufficient dynamic range and often provide limitations in readout speed, thereby limiting their use in applications where rapid decoding of brain activity is important.

SUMMARY

Disclosed herein are systems and methods for enabling a user to communicate using a brain computer interface (BCI) system through unspoken communications. As used hereafter, unspoken methods and/or unspoken communications refer to communications that can be performed by an individual through non-verbal (e.g., without verbal sounds), non-physical (e.g., not inputted by an individual through a physical means such as a keyboard, mouse, touchscreen, and the like), and/or non-expressive (e.g., not expressed through facial features, body language, and the like) means.

Generally, a BCI module interprets an individual's brain activity to characterize intentions of the individual in interacting with content in the environment of the user. In particular embodiments, the BCI module includes a flexible printed circuit assembly (FPCA) configured to conform to a head of a user, at least one emitter package, at least one detector package, and a controller. The emitter package includes at least one emitter configured to emit light towards the head of the user and the detector package includes at least one detector configured to detect light reflected from the head. Each emitter or detector of the BCI module is encased in a ferrule to direct light towards the head of the user and towards the detector. The controller is configured with electronics configured to provide power and/or computing functionality. The BCI module is configured in a wearable form factor that allows the user to repeatedly and reliably position light transmitting and light sensing components at the body region. As such, the system can include components appropriate for a small form factor that is portable and worn discreetly at a head region of the user.

Embodiments also relate to a sensor system for a brain computer interface (BCI) that enables detection and decoding of brain activity by optical tomography. The sensor system includes an array of pixels arranged as grouped pixel units to provide increased dynamic range. One or more of the grouped pixel units can operate in a saturated mode while providing information useful for decoding brain activity. Furthermore, the grouped pixel units are arranged to enable fast readout by a controller, thereby increasing detection and decoding ability by systems implementing the sensor design. The grouped pixel units of the sensor system are aligned with optical fibers of an interface to a body region of a user, where the optical fibers can be retained in position relative to the grouped pixel units by an optically transparent substrate that provides mechanical support while minimizing factors associated with divergence of light transmitted through optical fibers.

Embodiments also relate to a ferrule assembly in which a ferrule is mounted on a rigid section of a circuit board. An optical package including an optical element and a controller configured to operate the optical element are also mounted on the rigid section of the circuit board. Examples of optical elements may include an emitter, a detector, or a combination thereof. The ferrule is configured to optically couple to electronics for detecting brain signals, wherein the ferrule has optical properties to guide light between electronics and a user's head.

Embodiments of a flexible printed circuit assembly (FPCA) of a BCI module are configured to interconnect at least one emitter package to at least one detector package of the BCI module. The FPCA is comprised of rigid sections, each of which is configured to mount both emitter and detector package, and flexible sections, each of which is configured to connect at least two of the rigid sections. The geometry of the flexible sections enables the flexible sections to stretch to conform to the head of a user. The connection of the flexible sections to rigid sections of the FPCA enables the FPCA as a whole to stretch to confirm to the head of a user.

Embodiments also relate to decoding architecture that rapidly (e.g., in real time or near real time) decodes light-derived signals to extract predicted user actions or intents (e.g., commands) in relation to interactions with objects (e.g., virtual objects, physical objects), such that the user can manipulate the objects or otherwise receive assistance without manually interacting with an input device (e.g., touch input device, audio input device, etc.). The decoding architecture thus enables a neural decoding process with a neural signal stream as an input, and provides feedback to the user, where the feedback is used to train the neural decoding algorithm and user behavior. The neural signals can be blood oxygenation level dependent (BOLD) signals associated with activation of different articulators of the motor cortex, and signals can characterize both actual and imagined motor cortex-related behaviors. With training of the decoding algorithm, rapid calibration of the BCI for new users can additionally be achieved.

Figure 1A:
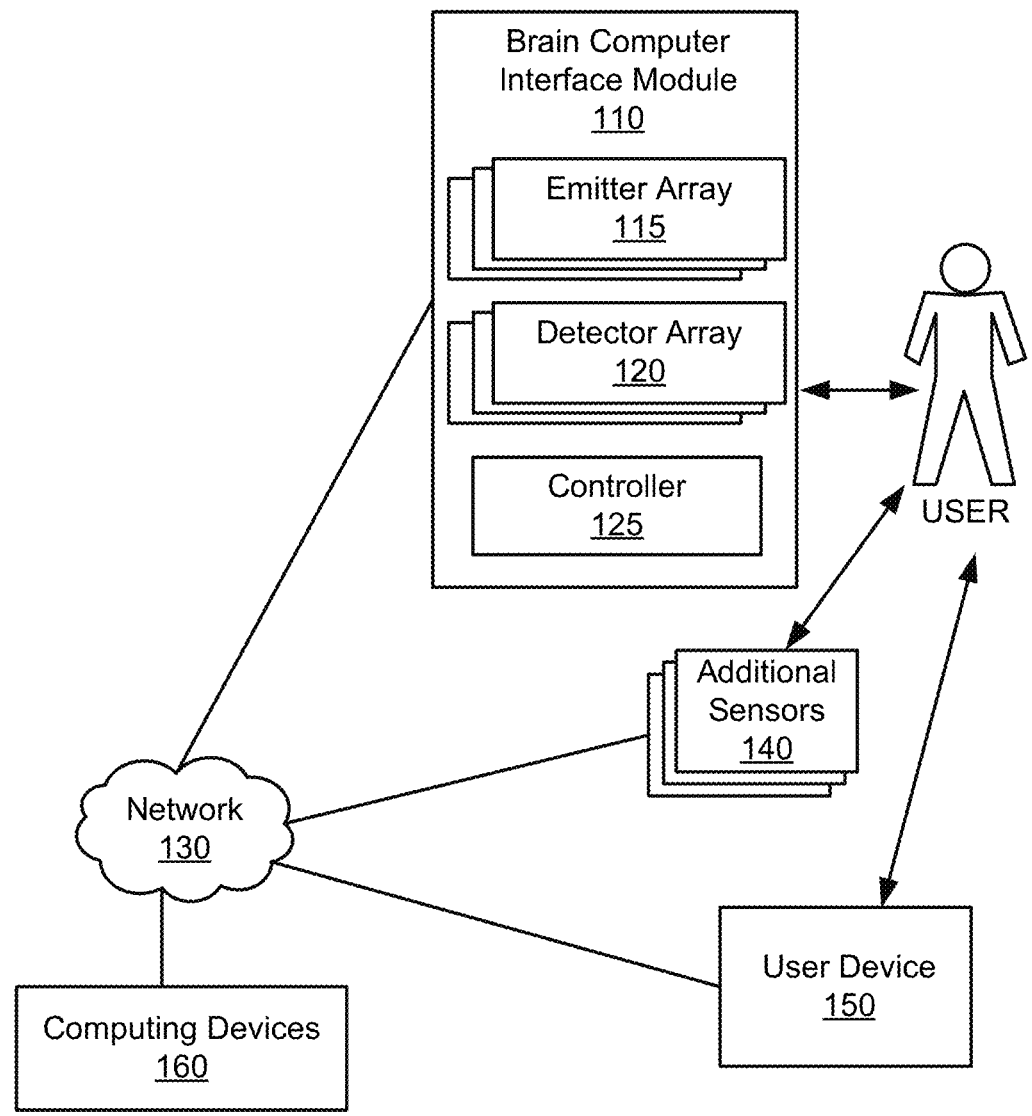
FIG. 1A is a block diagram of a BCI system for detecting and decoding brain activity of a user, according to an embodiment.

The figures depict various embodiments for purposes of illustration only. One skilled in the art will readily recognize from the following discussion that alternative embodiments of the structures and methods illustrated herein may be employed without departing from the principles described herein.

It is noted that wherever practicable similar or like reference numbers may be used in the figures and may indicate similar or like functionality. For example, a letter after a reference numeral, such as "150*a*," indicates that the text refers specifically to the element having that particular reference numeral. A reference numeral in the text without a following letter, such as "150," refers to any or all of the elements in the figures bearing that reference numeral (e.g. "computing component 150" in the text refers to reference numerals "computing component 150*a*" and/or "computing component 150*b*" in the figures).

DETAILED DESCRIPTION

1. Overview

Embodiments relate to a brain computer interface (BCI) including an interface module that transmits light from an emitter assembly to a body region of a user and receives light signals reflected from the body region of the user. The interface module additionally includes a controller that provides power to both the emitter and detector assemblies and computing functionality to covert the received light signals into one or more signals representing the user's brain activity. The BCI interface module is designed to be worn at a head region of a user and to generate optical signals that can be used to characterize brain activity of the user, where decoded brain activity can be used as inputs to control other systems and/or electronic content provided to the user.

In relation to brain activity sensing, embodiments also relate to an emitter array of the BCI, where the emitter array is provided in a miniaturized form factor that outputs light with appropriate characteristics to enable measurement of blood oxygenation by the detector array, where oxygenation levels can be determined relative to a reference state. In some embodiments, a detector array integrated into the BCI module is configured to measure other types of optical brain signals. The emitter array also includes individually addressable light emitters that cooperate with readout operations of one or more controllers associated with the detector array.

In relation to wearability, embodiments also relate to a wearable component that interfaces the emitter array and other system components to the head region of the user during use, in order to assess brain activity in a portable manner. The wearable component includes aspects that reliably bias optodes coupled to the emitter array and/or the detector array to the user's head as the user moves about in his or her daily life.

In relation to brain activity sensing and generation of outputs for optical tomography, embodiments also relate to a detector array that can be included with the BCI, where the sensor system enables detection and decoding of brain activity by optical tomography. In some embodiments, detection methodologies other than optical tomography may be used by the detector array. The sensor system includes an array of pixels arranged as grouped pixel units to provide increased dynamic range. One or more of the grouped pixel units can operate in a saturated mode while providing information useful for decoding brain activity. Furthermore, the grouped pixel units are arranged to enable fast readout by a controller (e.g., line scanner or an alternative controller), thereby increasing detection and decoding ability by systems implementing the sensor design. The grouped pixel units of the sensor system are aligned with optical fibers of an interface to a body region of a user, where the optical fibers can be retained in position relative to the grouped pixel units by an optically transparent substrate that provides mechanical support while minimizing factors associated with divergence of light transmitted through optical fibers.

2. System Environment

Figure 1B:
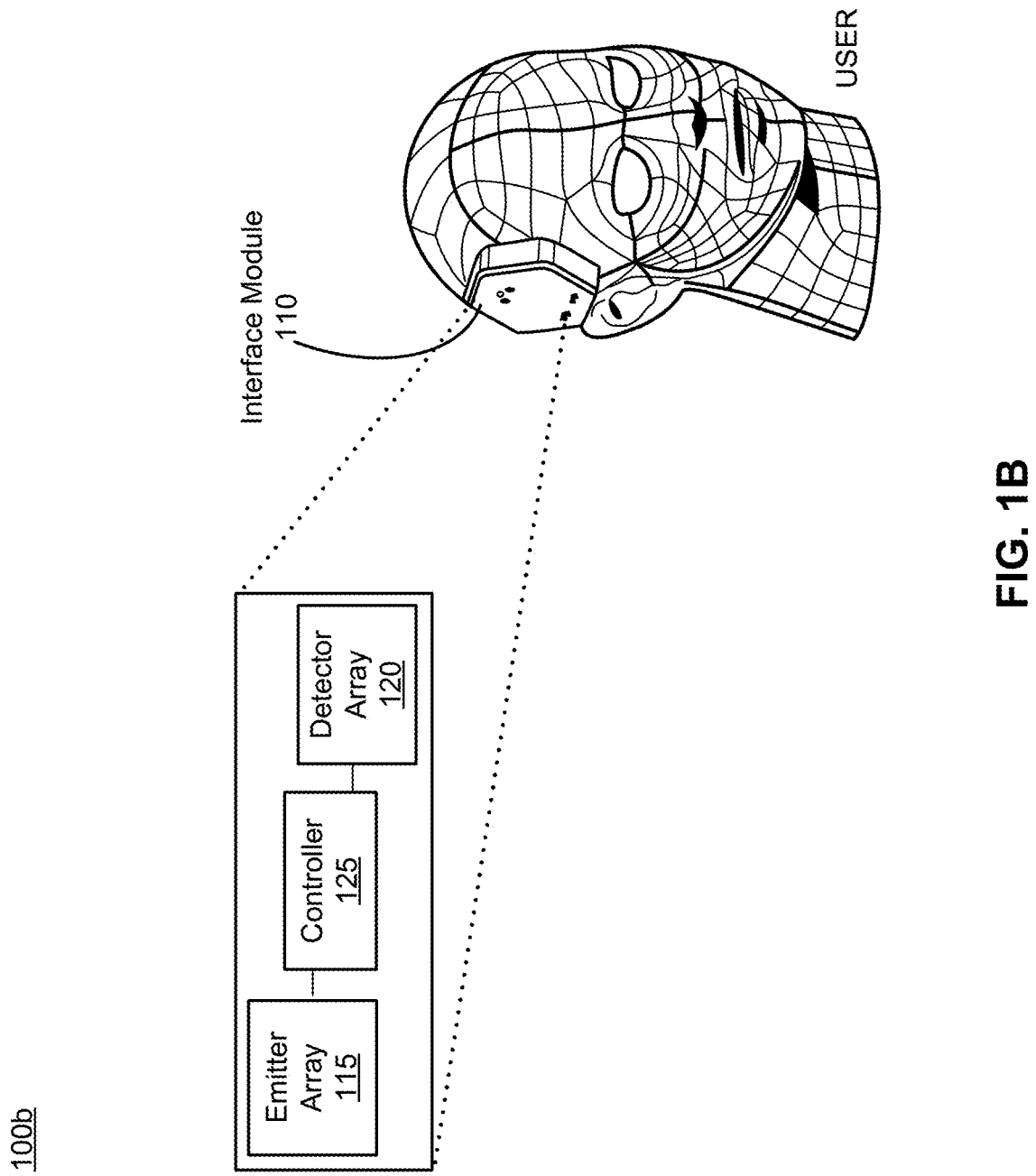
FIG. 1B is a schematic of an embodiment of the BCI module shown in FIG. 1A, according to an embodiment.

FIG. 1A is a block diagram of a brain computer interface (BCI) system for detecting and decoding brain activity of a user, according to an embodiment. FIG. 1B is a schematic of an embodiment of the BCI module shown in FIG. 1A, according to an embodiment. The system 100a includes a brain computer interface module 110, a network 130, additional sensors 140, a user device 150, and at least one computing device 160. The BCI module 110 further comprises an emitter array 115, a detector array 119, and a controller 115. By integrating both of the emitter array 115 and the detector array 110 into the BCI module 110, the BCI module 110 is configured to transmit light to a head region of a user and to receive light signals reflected from the head region of the user. The emitter array 115 and detector array 110 are coupled to a controller 115, which powers both arrays and processes and decodes neural stream signals for delivery of feedback to a user device 150 through a network 130.

As described in relation to other system components above and below, the BCI module 110 houses the emitter array 115, the detector array 110, and the controller 115. The housing is head-mountable for positioning the signal transmitting emitter array components at a head region. The housing may be composed of a polymer material and/or any other suitable materials. The BCI module 110 is thus designed to be worn by a user during use. Emitters of the emitter array 115 and sensors of the detector array 110 may be positioned and retained at the head region of the user through the interface module 110. Accordingly, the interface 110 is configured to enable characterization of brain activity from one or more regions of the user's brain through a non-invasive method. Specifically, the one or more of emitters of the emitter array 115 emit light and the one or more sensors of the detector array 110 capture light signals reflected from the head region of the user based on the emitted light. In some embodiments, the BCI interface module 110 is designed to fully cover the head of the user. In other embodiments, the BCI interface module is designed to cover a portion of the head, depending on the region(s) of interest associated with application for decoding brain activity.

In various embodiments, the emitter array 115 and detector array 110 enable optical tomography methods for receiving neural signals from the user, where the signals can be subsequently decoded and used for other applications (e.g., as control inputs that allow the user to control behavior of devices in his or her environment). Emitters of the emitter array 115 emit a signal that is absorbed and/or attenuated by neurons or networks of neurons in the region of the brain, and/or cause a physiological response that can be measured. Sensors of the detector array 110 detect a signal (e.g., backscattered light) from the same region of the brain. In one embodiment, the signal emitted by the emitters and captured by the sensors is light in the visible spectrum. Additionally, or alternatively, the signal emitted by the emitters of the emitter array 115 and captured by the sensors of the detector array 110 may be light in the non-visible spectrum.

The emitter array 115 communications with the controller 115 to receive instructions that enables the emitter array 115 to transmit light. The controller 115 may also function as a computing component of the system electronics. For example, the emitter array 115 receives inputs from the controller 115 and provides inputs to a particular emitter of the emitter array 115 to coordinate light emission from the emitter array 115 (e.g., in relation to operation of the detector array 110 in coordination with the emitter array 115). More specifically, the emitter array 115 receives instructions for transitioning the emitters between operation states (e.g., on states, off states) and/or within variations of operation states (e.g., a high power mode in the on state, a low power mode in the on state, etc.). The emitter array 115 and individual emitters are described in more detail below.

The detector array 110 detects the signals emitted by the emitter array 115 through the coupling of the sensors in the BCI interface module 110 to the user. The detector array 110 may also be in communication with the controller 115 to enable sensing, signal pre-processing, and/or signal transmission functions of the detector array 110. The detector array 110 may also be in communication with the controller 115 for computing functionalities, for example to support detection operation modes (e.g., sensor scanning modes) and/or other operation modes (e.g., signal transmission modes) of the detector array 110. In relation to sensors of the detector array 110, the sensors may include complementary metal oxide semiconductor (CMOS) architecture and/or another architecture, as described in more detail below.

The controller 115 encodes the reflected optical signals detected by the detector array 110 into signals which may be processed by one or more controllers associated with one or more of the computing device 160 and the user device 150.

The system 100 can additionally include other sensors 140 for detecting user behavior and/or other biometric signals that can supplement data processed by the BCI module 110. In some embodiments, the additional sensors 140 are also connected to the controller 115, which acts as a power component and/or a computing component to enable the additional sensors 140 to provide signals useful for decoding brain activity of the user, as described in more detail below.

In addition to the computing capabilities of the controller 115, the system 100a can additionally, or alternatively, implement other computing device 160 and/or a user device 150 to aid in particular computations or processing steps, for instance, through the network 130. Examples of computing devices 160 and/or user devices 150 include a personal computer (PC), a desktop computer, a laptop computer, a notebook, a tablet PC executing an operating system, for example, a Microsoft Windows-compatible operating system (OS), Apple OS X, and/or a Linux distribution. In other embodiments, the computing devices and/or user devices can be any device having computer functionality, such as a personal digital assistant (PDA), mobile telephone, smartphone, wearable computing device, or any other suitable computing device. The computing component 160 and/or other computing devices can execute instructions (e.g., computer code) stored on a computer-readable storage medium in order to perform the steps and processes described herein for enabling unspoken communications for control of other systems by a user. Collectively, the controller 115 and any other computing devices 160, with the network 130, can operate as a computing system for implementation of methods according to specific applications of use of the system 100.

In some embodiments, the computing devices 160 or the user device 150, or a controller (not shown) connected to the computing devices 160 or the user device 150, determines intentions of the user from signals provided by the detector array 110, where the intentions describe user wishes in relation to interacting with electronic content or a virtual assistant. In one embodiment, a computing device 160 determines the intentions that correspond to the neural signals that were gathered by the detector array 110 by applying a predictive model that is trained to predict intentions from neural activity. The computing device 160 may train the predictive model using training data including gathered experimental datasets corresponding to neural activity of previously observed individuals. Intentions can be decoded into communication related components (e.g., phonemes, words, phrases, sentences, etc.). In some related embodiments, computing device 160 enables a user to access an online social networking system, and therefore, allows users to communicate with one another through the online social networking system. As such, the computing device 160 may communicate on behalf of the individual through the network 130 with other computing devices (e.g., computing device 160, user device 150) of the social networking system. In some embodiments, the computing device 160 can communicate on behalf of the individual to other computing devices using the predicted phonemes, words, phrases, and/or sentences. In alternate embodiments, functionality described above with reference to the computing device 160 may be performed by a controller connected to a user device 150.

In addition to the configuration illustrated in FIG. 1B, multiple identical BCI modules 110 may be simultaneously placed on the head of a user with synchronous functionality. In another embodiment, multiple BCI modules 110 may be interlocked to operate in conjunction with various headset and head-mounted display designs.

The network 130 facilitates communications between the one or more computing devices. The network 130 may be any wired or wireless local area network (LAN) and/or wide area network (WAN), such as an intranet, an extranet, or the Internet. In various embodiments, the network 130 uses standard communication technologies and/or protocols. Examples of technologies used by the network 130 include Ethernet, 802.11, 3G, 4G, 802.16, or any other suitable communication technology. The network 130 may use wireless, wired, or a combination of wireless and wired communication technologies. Examples of protocols used by the network 130 include transmission control protocol/Internet protocol (TCP/IP), hypertext transport protocol (HTTP), simple mail transfer protocol (SMTP), file transfer protocol (TCP), or any other suitable communication protocol.

3. System—Neuroimaging Modalities

The system 100 described above operates to enable optical tomography or optical topography-associated modalities for decoding neural activity. The system 100 can characterize blood/tissue characteristics of the user through diffuse optical tomography/topography (DOT) modalities, in relation to characterizing cerebral blood flow, cerebral blood oxygenation, and/or other features indicative of brain activity. The system 100 can additionally or alternatively support other optical tomography or near-infrared spectroscopy approaches, including one or more of: functional near-infrared spectroscopy (fNIRS), functional time-domain near-infrared spectroscopy (TD-fNIRS), diffuse correlation spectroscopy (DCS), speckle contrast optical tomography (SCOT), time-domain interferometric near-infrared spectroscopy (TD-iNIRS), hyperspectral imaging, polarization-sensitive speckle tomography (PSST), spectral decorrelation, auto-fluorescence tomography, and photoacoustic imaging.

4. System Components 4.1 General System Architecture

Figure 2A:
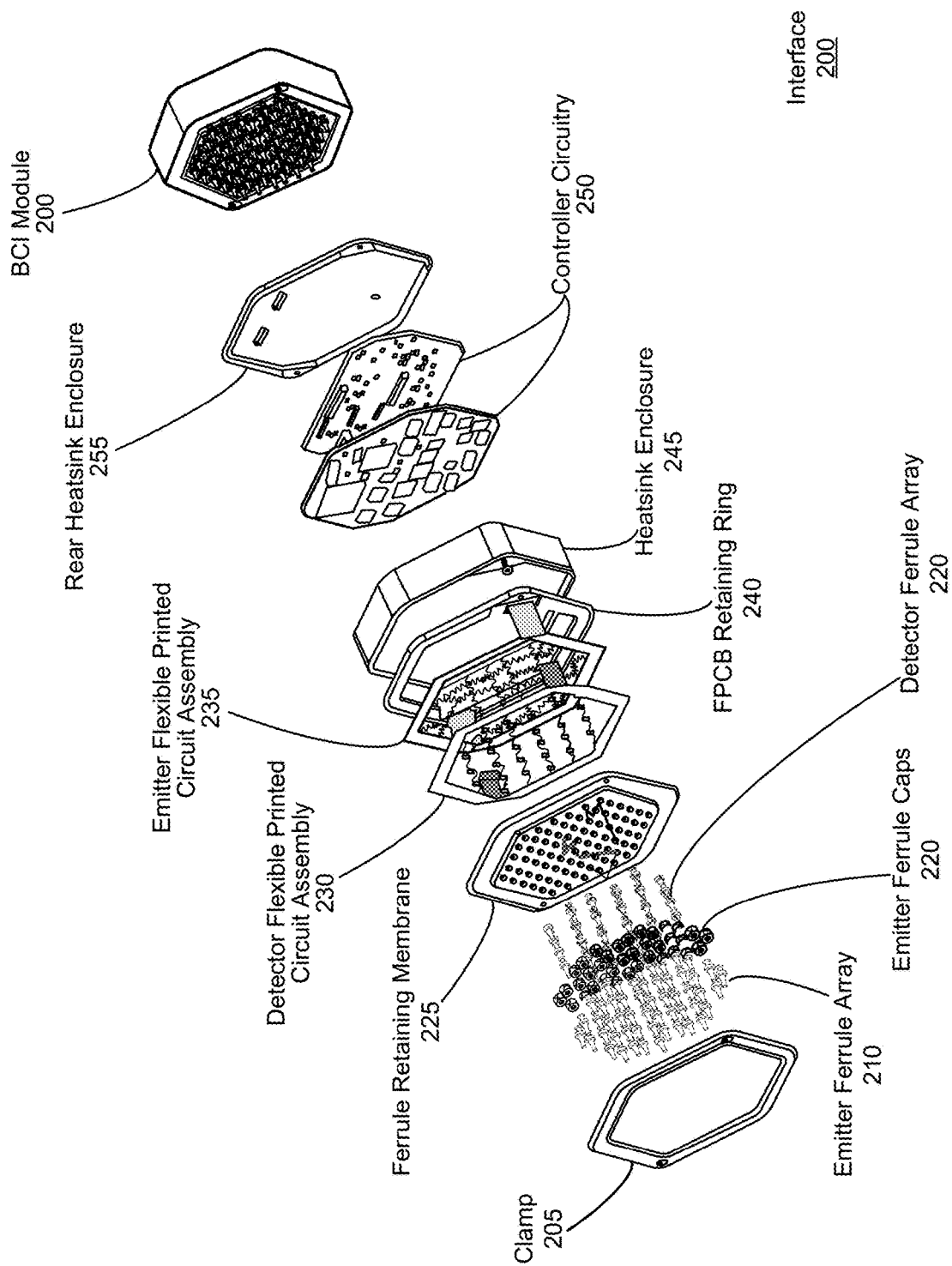
FIG. 2A-B are isometric views of components of the BCI module shown in FIG. 1B, according to an embodiment.

FIG. 2A is an isometric view of components of the BCI module shown in FIG. 1B according to an embodiment. The BCI module 200 includes optical components, which in combination form an emitter array 115 and a detector array 110, that are held between the clamp 205 and the heat sink enclosure 245. Electrical components, which in combination form a controller 115, are positioned between the heat sink enclosure 245 and the rear heatsink enclosure 255. This configuration allows for heat dissipation of the optical components to be independent from the heat dissipation of the controller 115. In other embodiments, the optical components and the controller 115 share the same heatsink and are housed together within the same housing.

The emitter array 115 includes a plurality of emitters and an emitter ferrule array 210. Each emitter of the emitter array 115 is configured to emit light towards the head of a user and is encased by an emitter ferrule of the emitter ferrule array 210. The emitted light travels through the ferrule onto the head of the user. In some embodiments, the emitter ferrule is a plastic casing. In alternate embodiments, the emitter ferrule may be designed using alternate or additional materials. Additionally, the optical components encased in a ferrule are sealed by a ferrule cap, which couples to an exposed end of the ferrule. Emitter ferrules of the emitter ferrule array 210 are coupled to emitter ferrule caps 215 in a one-to-one ratio.

Similarly, the detector array 110 comprises a plurality of detectors and a detector ferrule array 220. Detectors of the detector array 110 are configured to capture, via sensors, signals from the head region of a user based on light emitted by the emitter array 115. Each detector is encased by a detector ferrule of the detector ferrule array 220, which directs optical signals from the head of the user to the encased detector. In some embodiments, each detector ferrule of the detector ferrule array is coupled to a detector ferrule cap in a one-to-one ratio.

The BCI module 200 may additionally include a ferrule retaining membrane 225. The retaining membrane 225 is configured to couple each ferrule of the emitter ferrule array 210 and the detector ferrule array 220 and to hold each ferrule of the array in a fixed position. In some embodiments, the ferrule retaining membrane 225 is made of a stretchable material, for example a rubber material, that provides an elastic force allow both the emitter and detector ferrule arrays 210 and 220 to conform to the shape of the user's head. In alternate embodiments, the ferrule retaining membrane 225 is designed using a different material with similar elastic properties.

The BCI module 200 further comprises a detector flexible printed circuit assembly 230 and an emitter flexible printed circuit assembly 235. Both flexible printed circuit assembly (FPCA) 230 and 235 are designed to be sufficiently flexible, stretchable, or both to conform to the head of a user when the BCI module 200 is worn by the user. The FPCA 230 and 235 are designed with a combination of rigid sections and flexible sections. Ferrules of the emitter ferrule array are coupled to rigid sections of the emitter FPCA 235 and ferrules of the detector ferrule array are coupled to rigid sections of the detector FPCA 230. Each rigid section of the FPCA is connected to at least one flexible section. As will be discussed further with reference to FIGS. 7A-E, the configuration of the FPCA with multiple interconnected flexible and rigid sections enables the FPCA to conform to the shape of a user's head. For the sake of illustration, the detector FPCA 230 is configured with a different arrangement of flexible and rigid sections than the emitter FPCA 235. However, it is to be understood that the detector FPCA 230 and the emitter FPCA 235 may be designed with the same or a similar arrangement of flexible and rigid sections.

Each rigid section additionally includes electronics for emitting or detecting light. For instance, the electronics mounted on rigid sections of the emitter FPCA 235 may include an emitter package and control circuitry for emitting light through an emitter ferrule onto the head of a user. Moreover, electronics mounted on rigid sections of the detector FPCA 230 may include a detector package and control circuit for detecting light reflected from the head of the user. The FPCAs 230 and 235 include traces for routing signals between a controller (e.g., controller circuit 250) and the electronic components.

In some embodiments, the FPCAs 230 and 235 have multiple connectors to connect to a corresponding controller. For example, the detector FPCA 230 or the emitter FPCA 235 may have two connectors for connecting to a controller board to simplify or enhance the routing of the traces of the FPCA for connecting the electronic components to the controller.

The FPCA retaining ring 240 is configured to hold both of the detector FPCA 230 and the emitter FPCA 235 in place when the BCI module is worn by a user.

Between the heatsink enclosure 245 and the rear heatsink enclosure 255, the BCI module 200 includes a controller circuitry 250. In the illustrated embodiment, the controller circuitry 250 has a first circuit board with first connectors to connect to the detector FPCA 230 and a second circuit board with second connectors to connect to the emitter FPCA 235. Each circuit board of the controller circuitry additionally includes board-to-board connectors. In some embodiments, the controller circuitry may include a single circuit board configured to connect to both the detector FPCA 230 and the emitter FPCA 235.

Additional sensors may be mounted to the FPCA 235 adjacent to emitters of the emitter ferrule array 210 and detectors of the detector ferrule array 220. Examples of the additional sensors record measurements including, but not limited to, temperature measurements, inertial measurements, strain measurements, air pressure measurements, electrical voltage measurements, electrical current measurements, capacitance measurements, and impedance measurements.

The BCI module 200 is worn on the head of a user, for example as shown in FIG. 1B. The BCI module 200 is worn such that each ferrule of the emitter ferrule array 210 and the detector ferrule array 220 are in contact with the user's head. Because of the flexible properties of the FPCA's 230 and 235, the BCI module 200 can be worn on any part of the user's head to measure any region of the brain.

Figure 2B:
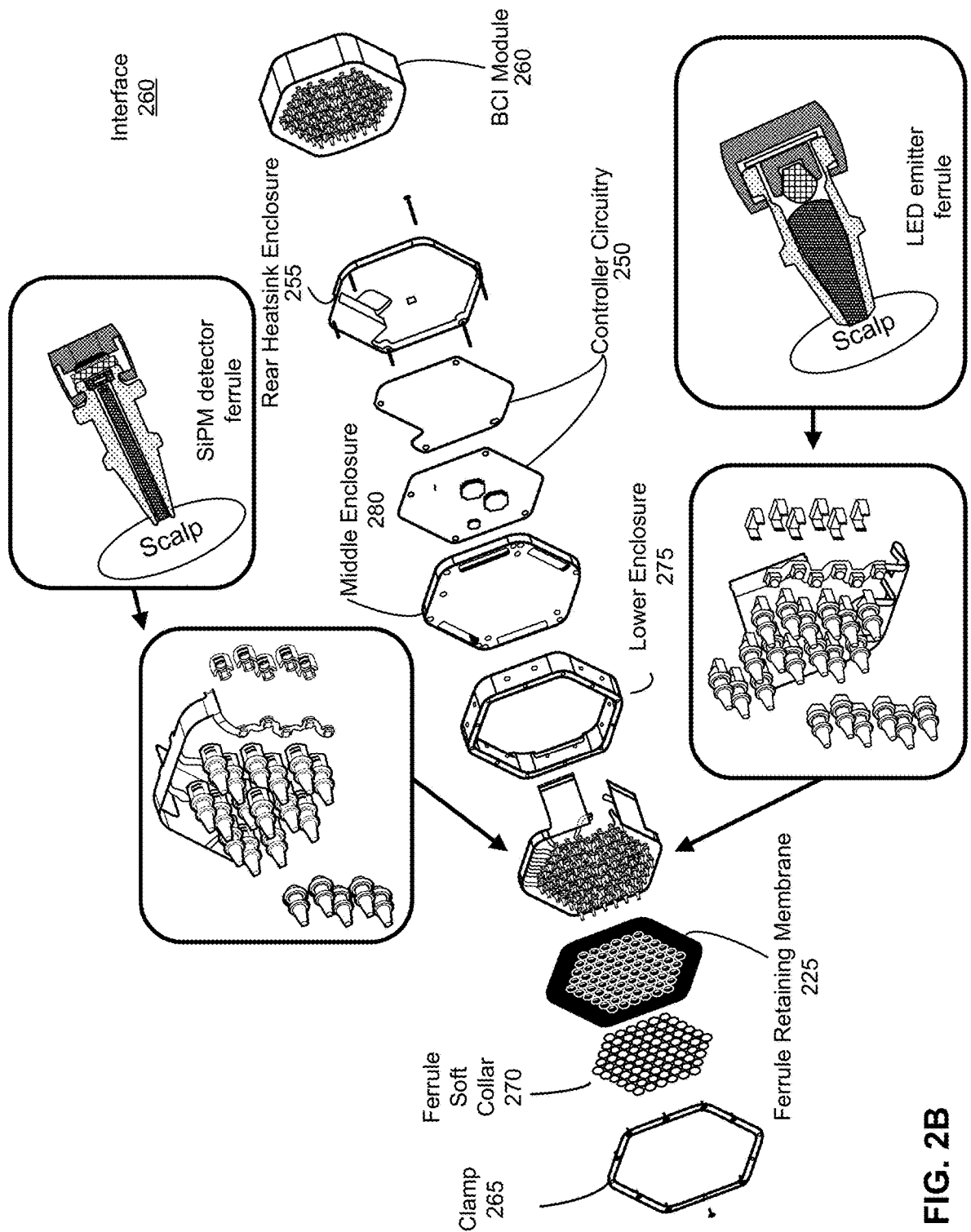

FIG. 2B is an isometric view of components of an alternative BCI module shown in FIG. 1B according to an embodiment. Components of the BCI module 255 may be functionally similar to those of the BCI module 200, but may differ in geometry. The BCI module 260 comprises a clamp 265 that encloses the skin-facing side of the BCI module 260. The clamp 265 is a design variant of the clamp 205 with a different geometry and screw count compared to the clamp 205. Additionally, the BCI module 260 includes a ferrule soft collar that provides an additional retention force to supplement the retention force provided by the ferrule retaining membrane 225.

As illustrated in the extruded views of the detector array and the emitter array, the emitter ferrule caps and the detector ferrule caps may differ in design and geometry to accommodate the varying designs of control electronics for the emitter or detector array. Compared to the heat sink enclosure 245 illustrated in FIG. 2A, the BCI module 255 may include two separate components: a lower enclosure 275 with mounting features to hold the flexible printed circuit assembly in position and a middle enclosure 280. Additionally, components of the controller circuitry 250 in the BCI module 260 are geometrically different from the same components in the embodiment illustrated in FIG. 2A.

4.2 Emitter Array

As described above, the BCI module 200 includes an array of emitters, each of which is encased in a ferrule of the emitter ferrule array 210. The emitter(s) function to emit light having suitable parameters, where the light interacts with a region of interest (e.g., the head region of the user), and is subsequently transmitted to a detector array (described below) for characterization of the region of interest. As described herein, optical assemblies involving an emitter of an emitter array and/or additional optical components are referred to as emitter assemblies. Each emitter ferrule encases an emitter package. In some embodiments, each emitter ferrule additionally encases a controller or a portion of the controller configured to operate the emitter package.

The emitter package includes laser light emission elements but can include light emitting diode (LED) elements or other types of light emitters in alternative embodiments. In relation to laser light emission elements, the emitter package can include vertical cavity surface emitting laser (VCSEL) elements with semiconductor architecture for perpendicular beam emission. Use of VCSEL elements contributes to a compact light emission configuration that provides suitable power for wearable applications requiring high power light output for optical detection of characteristics of a multidimensional region of interest (e.g., a head region of a user). In relation to laser light emission elements, the emitter array can alternatively include emitters with conventional semiconductor architecture for edge beam emission from surfaces cleaved from a semiconductor wafer.

In some embodiments, emitters are configured to emit light in the visible spectrum. In other embodiments, emitters are configured to emit light in the non-visible spectrum. For BCI applications involving characterization of brain activity, the emitters include emitters configured to emit red wavelength light and near-infrared light. However, in alternative variations, the emitters are configured to emit only a single wavelength of light, or other wavelengths of light.

Each emitter of the emitter array has its own die physically coupled to an electronics substrate (e.g., emitter FPCA 235) of system electronics, such that the emitter is individually addressable in a compact format. In some embodiments, each emitter is packaged into an individual integrated circuit package or chip and mounted on the substrate to be interconnected with other components of the BCI module 200. In relation to addressability, each emitter is transitionable between an activated state for emitting light (with different output settings) and a deactivated state. However, in alternative variations, multiple emitters can be associated with a single die physically coupled to an electronics substrate 223 to enable addressability of emitters in groups, or multiple emitters of the emitter array 210 can be associated with a single die physically coupled to the electronics substrate 223. In alternative embodiments where each emitter does not have its own die, the emitters can, however, still be individually addressable using other wiring architecture.

The emitters may operate in a continuous emission mode for continuous emission of light. The emitters may also operate in a pulsed mode, where periods of light emission are interspersed with periods of non-emission at a desired frequency. Pulses can thus be associated with one or more of: a pulse profile having width characteristics and other pulse shape aspects (e.g., peaks, troughs, etc.); power draw (e.g., in relation to power amplitude); temporal features (e.g., periodicity, frequency of pulses, etc.); and any other suitable pulse features. For example, the emitters operate in a pulsed mode with pulse width modulation (PWM) having a power draw of 27% efficiency at 100 mW of power output.

Figure 3:
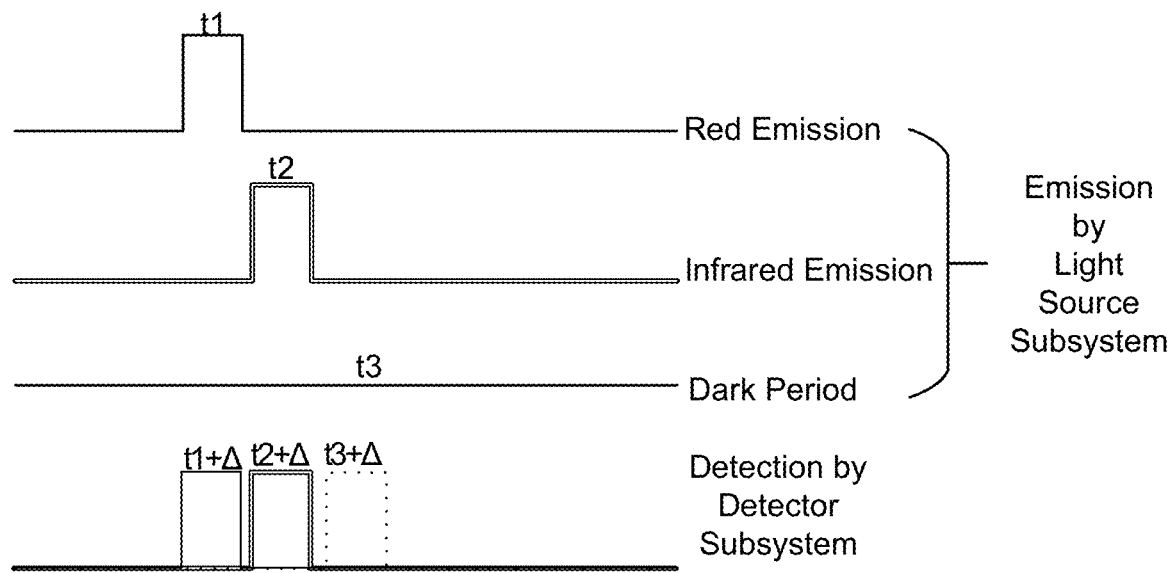
FIG. 3 illustrates an example of light emission operation in relation to signal detection, according to an embodiment.

In relation to non-continuous transmission modes, light emission by emitters may be coordinated with detection by the detector array, where emission of light (e.g., by a subset of emitters) is timed with light detection in phases. In one example, as shown in FIG. 3, the emitters of the emitter array emit a first light profile (e.g., a pulse of red light provided within a first time window), followed by a second light profile (e.g., a pulse of infrared light provided within a second time window), followed by a third light profile (e.g., dark period provided within a third time window), where each pulse and dark period is detected sequentially by an embodiment of the detector array described below. As such, scanning by the detector array to generate and decode light signal data can be carefully timed with operation of the emitter array.

Emitters may further be configured to transmit light through optical elements that manipulate light along a path of transmission to a surface of the region of interest. Optical elements can include one or more of: filters, lenses, mirrors, collimation elements, waveguides, other beam shaping elements, and any other suitable optics.

Figure 4A:
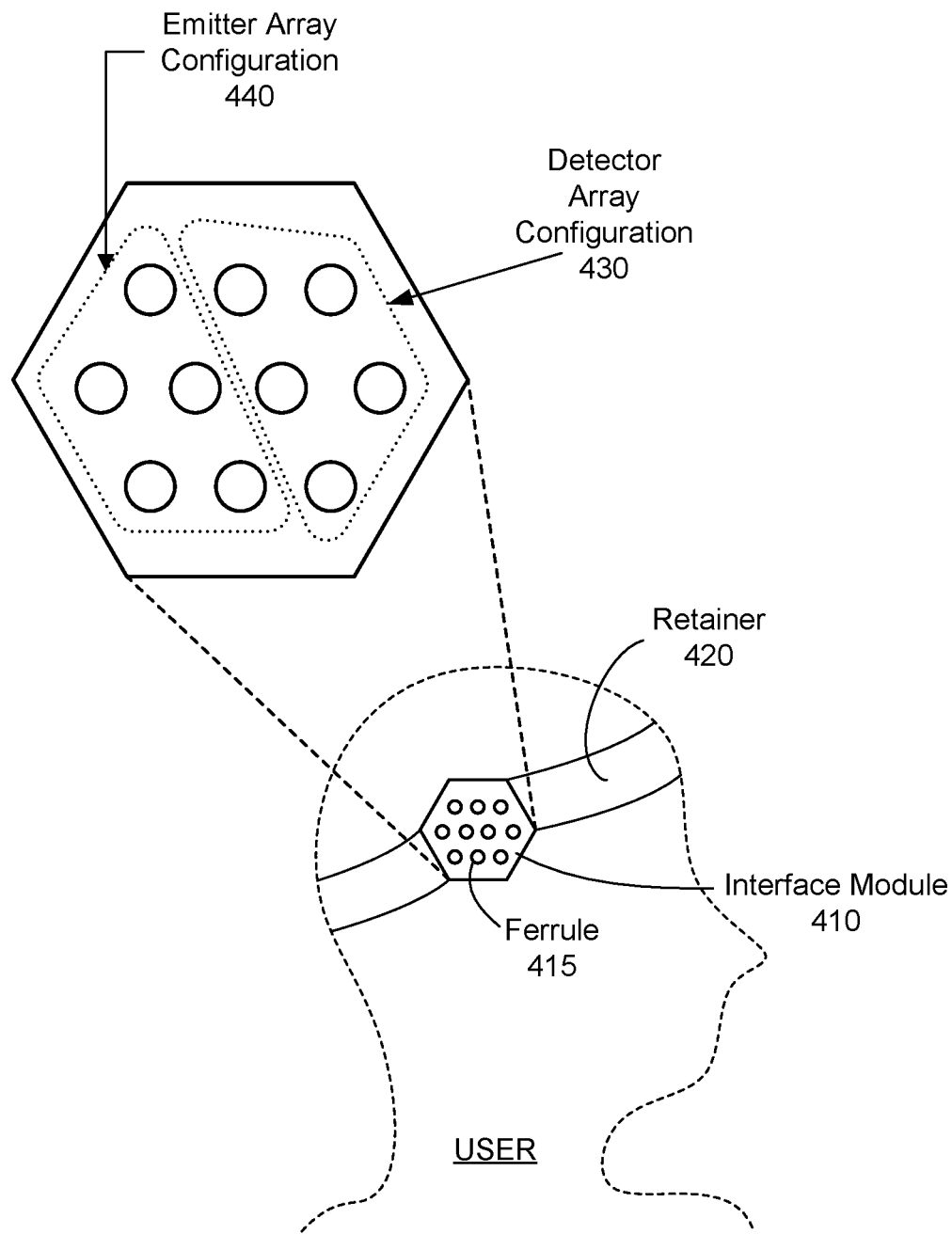
FIGS. 4A-C illustrate example configurations of emitter and detector arrays in a BCI module, according to an embodiment.
Figure 4C:
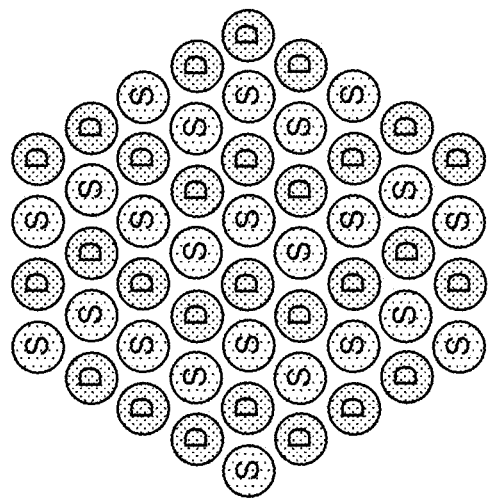
Figure 4B:
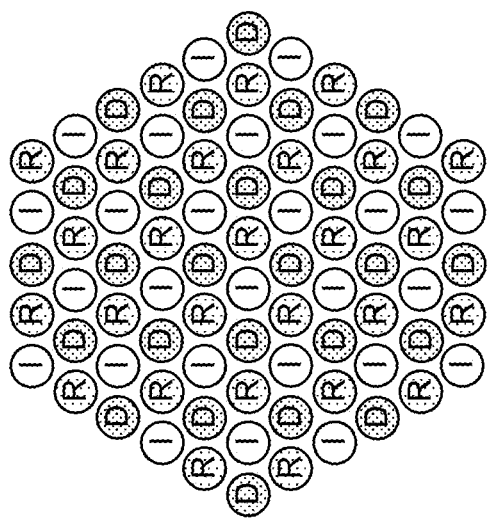

FIGS. 4A-C illustrate example configurations of emitter array 115 and detector array 110 in a BCI module, according to an embodiment. FIG. 4A depicts a head-mountable interface according to an embodiment, where the interface module 410 functions to interface light emitters of the emitter array 115 (such as an embodiment of the emitter array described above) to the head region of the user during use, and to interface the head region with a detector array (described in more detail below), in order to assess brain activity in a portable manner. The interface module 410 is configured to be worn by a user and includes an array of ferrules 415. The interface module 410 is secured to the head of the user (or another body region of the user, in relation to signal detection from other body regions) by a retainer 420.

The emitters of the emitter array are arranged in a 2D array. The 2D array may be a square array, where the square array can have equal numbers of emitters along its width and height. The size of the array of emitters, in terms of number of emitters, distribution of emitters in space, and spacing between emitters, can be configured based on size of each individual emitter (in relation to size constraints of the wearable system). In alternative embodiments, however, the emitters are arranged in a polygonal array, ellipsoidal array, or in any other suitable manner (e.g., an amorphous array). FIG. 4A illustrates an exemplary configuration 440 of an emitter array and an exemplary configuration 430 of a detector array, according to an embodiment. In the illustrated embodiment of FIG. 4A, the emitter array configuration 440 and the detector array configuration 430 are separated into distinct sections of the interface module 410. However, in alternate embodiments, the emitter array configuration and the detector array configuration may overlap such that emitters and detectors are positioned in the same region of the interface module 410. Additionally, the configuration 430 of the detector array mirrors the configuration 420 of the emitter array. However, in alternate embodiments, the configuration 430 may be different from the configuration 420.

In most embodiments, the emitter array and detector array are designed with dual wavelength functionality, for example to emit and detect red and infrared light. Because red and infrared light scatters in different ways, a controller in a BCI module may generate a positive image and a negative image, which would allow the BCI system to verify a signal reading with different views. In the embodiments of FIGS. 4B and 4C, the emitter array and detector array are arranged in a hexagonal pattern with a mechanical symmetry. Within each array, optical components (i.e., emitters or detectors) are arranged with a uniform spacing, orientation, and distance. Accordingly, FIG. 4B illustrates an implementation in which a first subset of emitters of the emitter array are instructed to emit infrared and a second subset of the emitters are instructed to emit red light. Each detector of the detector array is surrounded by six emitters: three emitters configured to emit red light and three emitters configured to emit infrared light. FIG. 4C illustrates an alternate implementation in which each emitter of the emitter array is configured to emit a combination of red and infrared light. The configuration of FIG. 4C allows a single emitter to emit both infrared and red light, which in turn enables the number of detectors on the BCI module to be maximized.

4.3 Integrated Ferrule Assembly

As described herein, an integrated ferrule assembly comprises a ferrule, which is mounted to an FPCA that is configured to conform a head of a user. The ferrule encases electronics that includes, but is not limited to, an optical element (e.g., a sensor of a detector array or an emitter of an emitter array) and a controller (i.e., control electronics) configured to operate the optical element. In implementations in which the optical element is an emitter, the controller generates instructions for the emitter to emit infrared, red, or both light towards the head of the user. In such implementations, the ferrule channels light from the emitter towards the head. Alternatively, when the optical element is a sensor, the controller provides instructions for the sensor to detect light reflected off the head and the ferrule channels the light reflected off the head of the user to the detector.

Figure 5A:
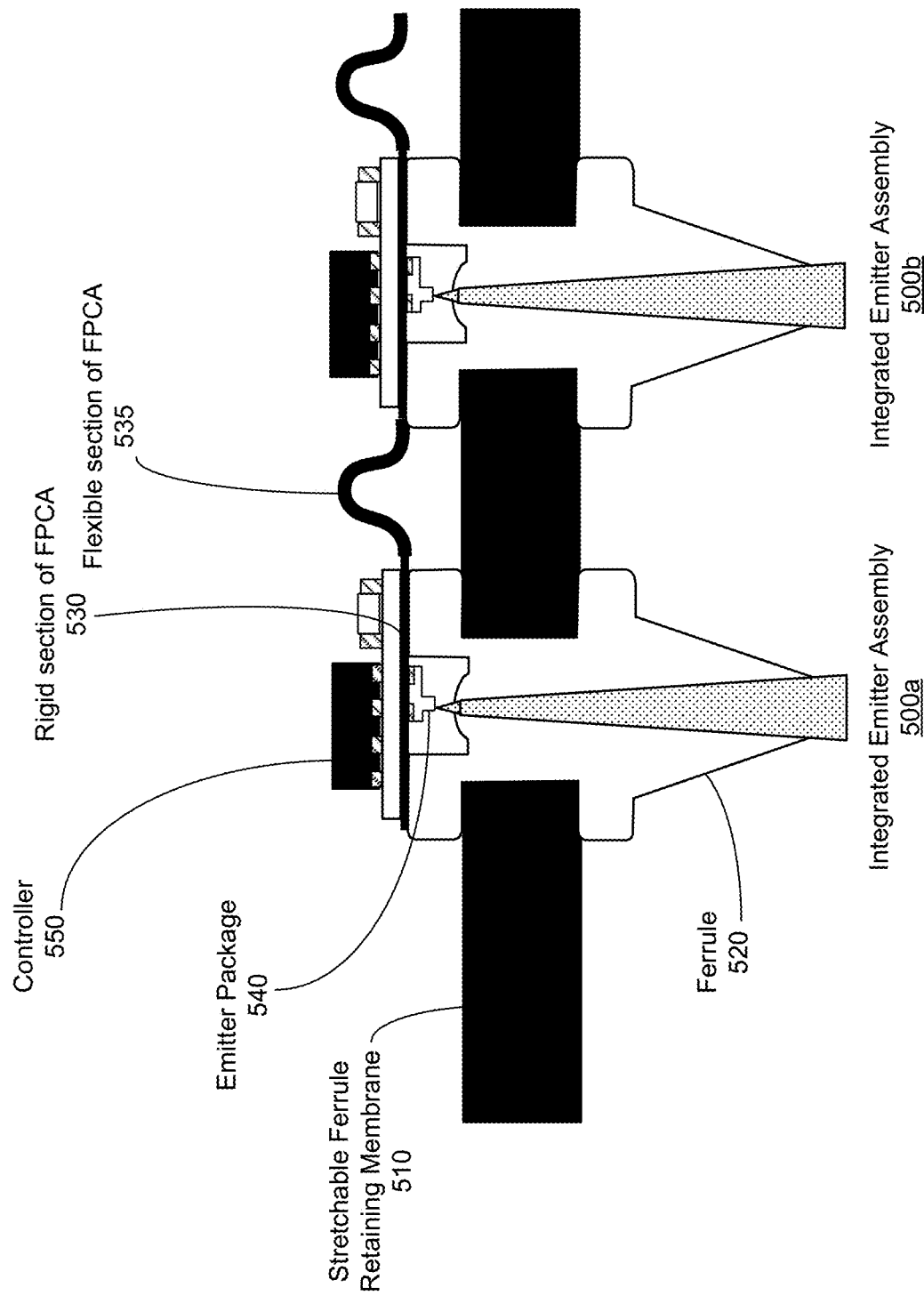
FIG. 5A is a cross-sectional schematic of an integrated emitter assembly, according to an embodiment

As described herein, optical packages involving an emitter of the emitter array 115 and/or additional optical components are referred to as emitter packages. FIG. 5A is a cross-sectional view of an integrated emitter assembly, according to an embodiment. The emitter assembly is configured to emit light towards the head of the user. The integrated emitter assembly 500 includes a rigid section 530 of an FPCA. Additionally, an emitter package 540 and a controller 550 are attached to the rigid section 530 of the FPCA. The rigid section 530 of the FPCA then connects the emitter package 540 and the controller 550 to each other. In some embodiments, the emitter package 540 and the controller 550 are attached to different sides of the rigid section 530 of the FPCA. The emitter package 540 is mounted to a side of the rigid section 530 of the FPCA such that, when worn by a user, the emitter package 540 emits light towards the head of the user. The emitter package 540 includes an optical element, for example a vertical cavity surface emitting laser (VCSEL), a single wavelength LED, a dual wavelength LED, an alternate suitable emitter component or a combination thereof, configured to emit light towards the head of a user. Moreover, as described above, the controller 550 generates instructions for the emitter package to emit light.

The integrated emitter assembly 500 further includes a ferrule 520 which encases the emitter package 540. In some embodiments, the ferrule 520 encloses additional components mounted on the same side of the rigid section of the FPCA as the emitter package 540. Although not shown, the integrated emitter assembly 500 may further include a ferrule cap to seal the emitter package 540 and controller 550 in position within the ferrule 520 and to secure the ferrule 520 against the rigid section 530 of the FPCA. The ferrule 520 is attached to a stretchable ferrule retaining membrane 510, which is configured to stretch and flex to conform to the head of a user. When a BCI module is worn by a user, the stretchable ferrule retaining membrane 510 secures individual ferrules of each of the integrated emitter assemblies 500 in a fixed position against the head of the user.

An integrated emitter assembly 500a is physically and electrically coupled to at least a neighboring integrated emitter assembly 500b by a flexible section 535 of the FPCA. In some embodiments, an integrated emitter assembly 500a is coupled to multiple neighboring integrated emitter ferrule assemblies 500 through multiple flexible sections 540 of the FPCA. The flexible section 535 of the FPCA allows each of the integrated emitter assemblies 500 to move independently from each other, while maintaining physical or electrical connection with each other. As such, the flexible section 535 of the FPCA allows for electrical signals to be routed to each of the individual integrated emitter assemblies 500 while allowing the integrated emitter assemblies 500 to move independently to conform to the shape of a user's head.

Figure 5B:
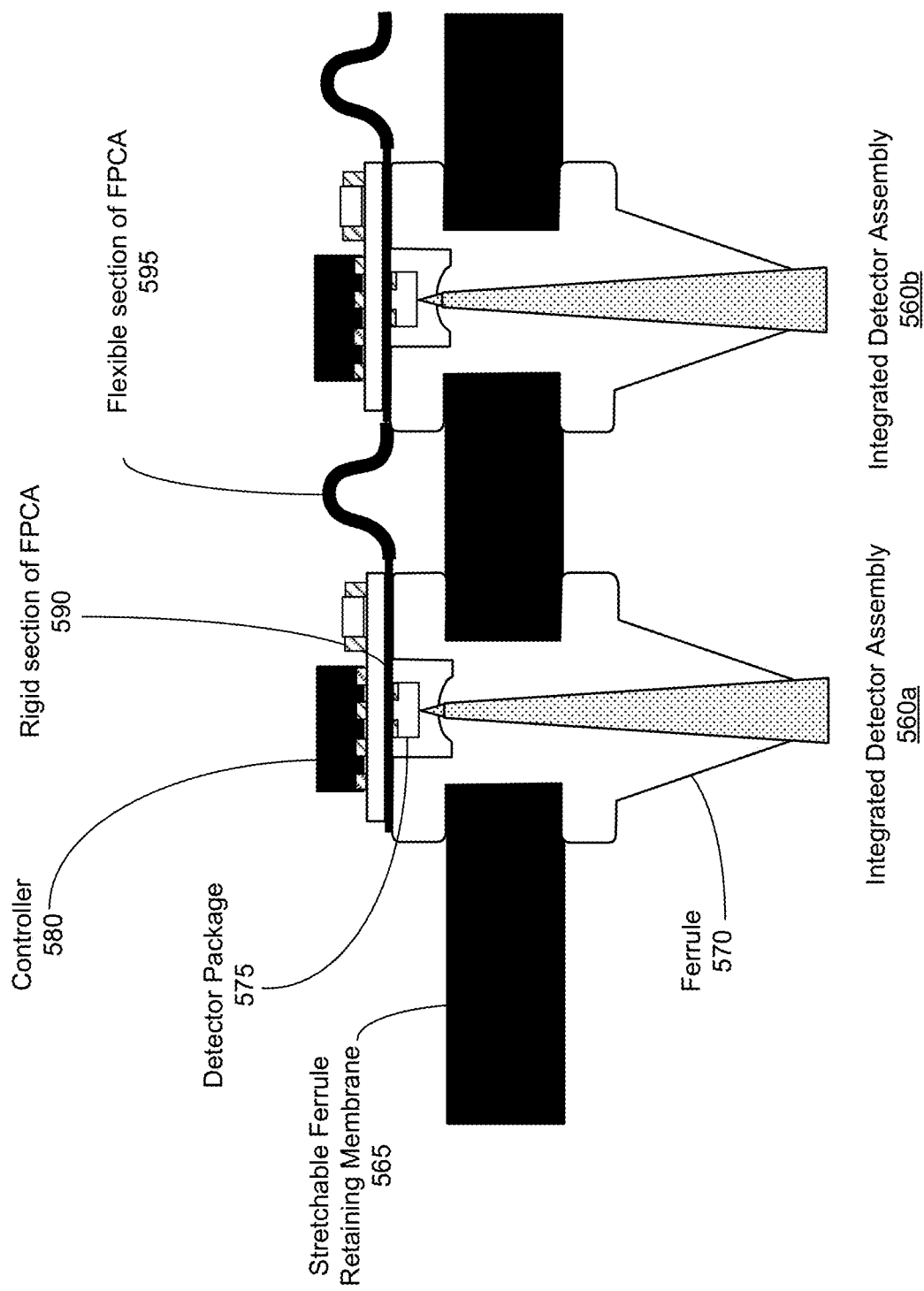
FIG. 5B is a cross-sectional schematic of an integrated detector assembly, according to an embodiment.

As described herein, optical packages involving a sensor of the detector array 110 and/or additional optical components are referred to as detector packages. FIG. 5B is a cross-sectional view of an integrated detector assembly, according to an embodiment. In comparison to the integrated emitter assembly 500, the integrated detector assembly 560 is configured to direct light reflected off the head of a user towards a detector package. The integrated detector assembly 560 includes a rigid section 590 of an FPCA. Additionally, a detector package 580 and a controller 590 are attached to opposite sides of the rigid section 590 of the FPCA. The rigid section 590 of the FPCA then connects the detector package 575 and the controller 580 to each other. In some embodiments, the detector package 575 and the controller 580 are attached to different sides of the rigid section 590 of the FPCA. The detector package 575 is mounted to a side of the rigid section 590 of the FPCA such that, when worn by a user, the detector package 575 is pointed towards the head of the user. The detector package 575 includes an optical element, for example a silicon photomultiplier, an alternate suitable optical sensor, or a combination thereof, configured to detect an optical signal. As described herein, a silicon photomultiplier is a light sensor based on semiconductor technology that is capable of detecting very small light intensity at a photon-level. The silicon photomultiplier may additionally consist of microcells, each of which is charged with high voltage. When a microcell is triggered by detection of a photon, a predetermined discharge current is generated and flows to a resistor to generate the voltage output. In some embodiments, the amplitude of the voltage output is proportional to the number of triggered microcells. Moreover, as described above, the controller 580 generates instructions for the detector package 575 to start detecting light, receives optical signals detected by the detector package 575, and encodes the detected optical signal to be sent to a computing device for analysis.

The integrated detector assembly 560 further includes a ferrule 570 which encases the detector package 575. In some embodiments, the ferrule 570 encloses additional components mounted on the same side of the rigid section of the FPCA as the detector package 575. Although not shown, the integrated detector assembly 560 may further include a ferrule cap to seal the detector package 575 and the controller 580 in position within the ferrule 570 and to secure the ferrule 570 against the rigid section 590 of the FPCA. The ferrule 520 is attached to a stretchable ferrule retaining membrane 565. When a BCI module is worn by a user, the stretchable ferrule retaining membrane 565 secures individual ferrules of each of the integrated detector assemblies 560 in a fixed position against the head of the user.

An integrated detector assembly 560a is physically and electrically coupled to at least a neighboring integrated detector assembly 570b by a flexible section 595 of the FPCA. In some embodiments, an integrated detector assembly 560a is coupled to multiple neighboring integrated detector ferrule assemblies 570 through multiple flexible sections 595 of the FPCA. The flexible section 595 of the FPCA allows each of the integrated detector assemblies 560 to move independently from each other, while maintaining physical or electrical connection with each other. As such, the flexible section 595 of the FPCA allows for electrical signals to be routed to each of the individual integrated detector assemblies 560 while allowing the integrated detector assemblies 560 to move independently to conform to the shape of a user's head.

Figure 6B:
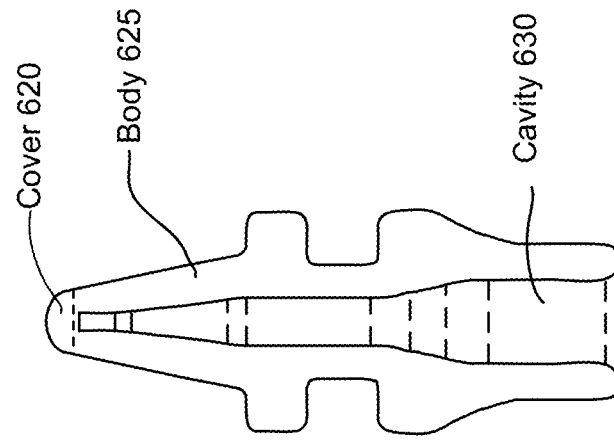
FIGS. 6A-6K are several perspective views of a ferrule, according to an embodiment.
Figure 6A:
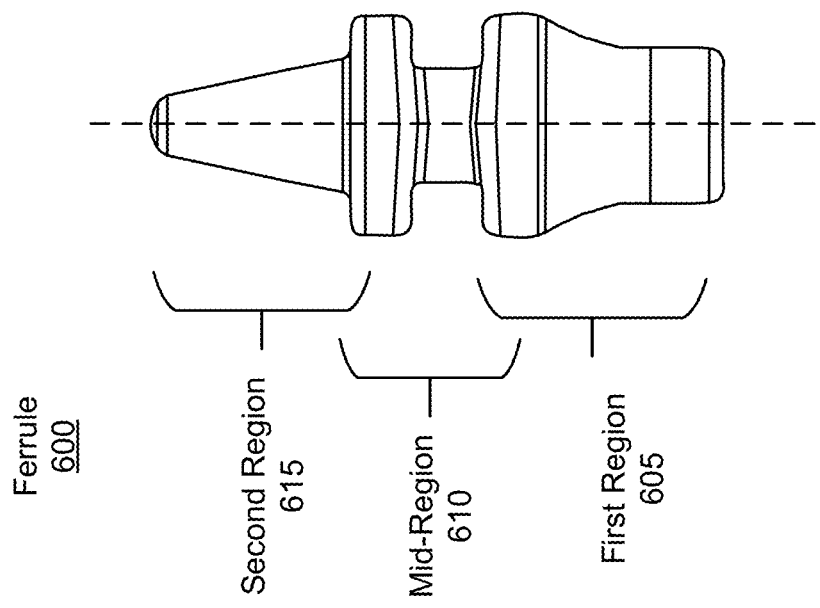

FIG. 6A is a side view schematic of a ferrule, according to one embodiment. FIG. 6A shows a ferrule 600 that can be retained by the stretchable ferrule retaining membrane 510 (or the stretchable ferrule retaining membrane 565). The ferrule 600 has a first region 605 and a second region 615 that are joined at a mid-region 610, where the width of the ferrule 600 is reduced at a mid-region 610 such that the ferrule 600 can interlock with a port. in some embodiments, the ferrule 600 has a varying width along the length of the body 625. The width of the ferrule 600 is smallest at the end of the second region 615 such that the end of the second region 615 can comfortably interact with a head region of a user. In alternative embodiments, the ferrule 600 can have a constant width along the length of the body 625 and be coupled to the cap in another manner, as described above. The ferrule 600 can also have wider or smaller end regions, depending on the design considerations of the system (e.g., manufacturability, size, material, etc.).

FIG. 6B is a cross-sectional view of the ferrule illustrated in FIG. 6A, according to one embodiment. The illustrated ferrule includes a body 625 and a cavity 630. The cavity 630 terminates within the second region 615 of the body 625. Alternatively, the cavity 630 can extend through the first region 605 and the second region 615 of the ferrule 600. The ferrule 600 can include a cover 620 coupled to the body 625 and/or other components within the cavity 630. The cover 620 can function to seal the cavity 630 from the external environment in order to protect internal components. The cover 620 can also function as the interface between the user and the ferrule 600. The cover 620 can be a separate component coupled to (e.g., by an adhesive, interlocking mechanism, etc.) or ensheathing the body 625. Alternatively, the cover 620 can be a continuous piece of the body 625.

The cover 620 can also be made of a material that provides light manipulation functions. For instance, the cover 620 can be composed of an optically transparent material that allows light transmission without significant loss. In another embodiment, the cover 620 can be made an optically translucent material to facilitate diffusion of stimulation light. In another embodiment, one or more regions of the cover 620 can include lenses that affect light transmission through or into the cover. The ferrule 600 may be designed using optical grade acrylic or polycarbonate, or any other suitable material. Additionally, in some embodiments, a physical vapor deposition coating is applied to the ferrule 600 to prevent light from leaking from the ferrule 600.

The cavity 630 is configured to house an optical package, for example an emitter package of an integrated ferrule assembly or a detector package of an integrated detector assembly. The cavity 630 is designed with a volume that allows the ferrule to be placed on top of the entirety of the optical package. Depending on the design of the optical package, the geometry of the cavity 630 may vary to accommodate differently shaped elements of the optical package, for example sensors or detectors of varying sizes and shapes. Additionally, the cavity 630 may be designed to channel light toward or away from the optical package without obstructing or affecting the intensity of the channeled light.

In morphology, the ferrule 600 may be held in position by a ferrule retaining membrane, for example the ferrule retaining membrane 225. In some embodiments, the body 625 has a recessed ring about its external perimeter that forms a portion of an interlocking mechanism such that it can mate with a port of an array of ports in the ferrule retaining membrane, for instance, where the port includes a protrusion about one or more portions of its internal perimeter, the protrusion operable to lock with the recess of the body 625. The width of a middle portion of the body 625 may be smaller than one or both end regions of the body 625 such that the ferrule 600 is retained in position without an adhesive or other attachment mechanism. In an alternative embodiment, the body 625 of a ferrule 600 has a constant width. In still other embodiments, the body 625 may be cylindrical, polygonal, or any other suitable shape for encasing control electronics and directing light.

The ferrule 635 may be made of a single material or a composite material with physical properties capable of supporting the optical fiber 642. The material can have mechanical properties (e.g., ductility, strength) suited support the optical fiber 642. In relation to mechanical properties, the material(s) of the ferrule 635 can have a compressive strength, a shear strength, a tensile strength, a strength in bending, an elastic modulus, a hardness, a derivative of the above mechanical properties and/or other properties that enable the ferrule 635 to move with respect to the stretchable ferrule retaining membrane 510 while maintaining its position relative to other ferrules of a BCI module. The ferrule 635 may be made of polycarbonate; however, the body can be made of another material (e.g., polymeric material, non-polymeric material).

In relation to electrical properties, the material(s) of the ferrule 635 can have a conductivity, resistivity, a derivative of the above electrical properties and/or other properties that support signal transmission through the embedded optical fiber 645. The ferrule 635 may be made of an insulative material in order to prevent excess noise from propagating from the emitter package to the user and/or to other components of the system.

In relation to optical properties, the material(s) of the ferrule 635 can have optic properties that enable signal transmission through the embedded optical fiber 645. The ferrule 655 can include an optically opaque adhesive configured to facilitate signal transmission between the first region 605 and the second region 615 of the ferrule 600. The body 625 of the ferrule can also be composed of an optically opaque adhesive. In alternative embodiments, the ferrule 600 can be composed of any suitable material.

Figures 6C, 6D, 6E:
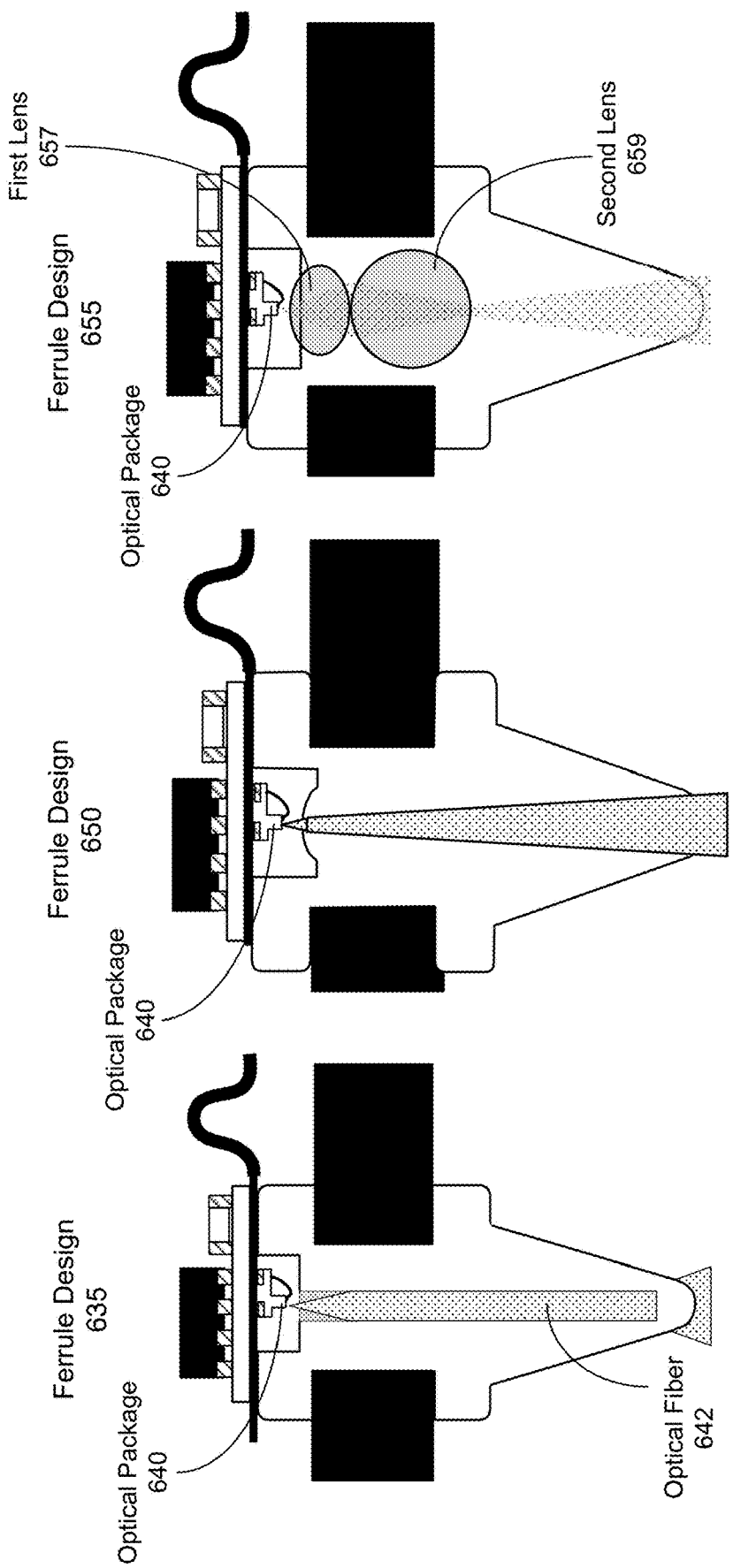

FIGS. 6C-6E illustrate alternate ferrule designs. FIG. 6C illustrates a ferrule design 635 in which an optical fiber 642 is embedded into the ferrule 635 to guide emitted and reflected light to and from the optical package 640. The optical fiber 642 may vary in length depending on the design of the ferrule. The illustrated embodiment of FIG. 6C may be implemented to direct light from the head of a user towards a detector assembly or from the emitter assembly to the head of the user. The body of the ferrule may be cylindrical, polygonal, or any other suitable shape for supporting the embedded optical fiber 642.

Figure 6G:
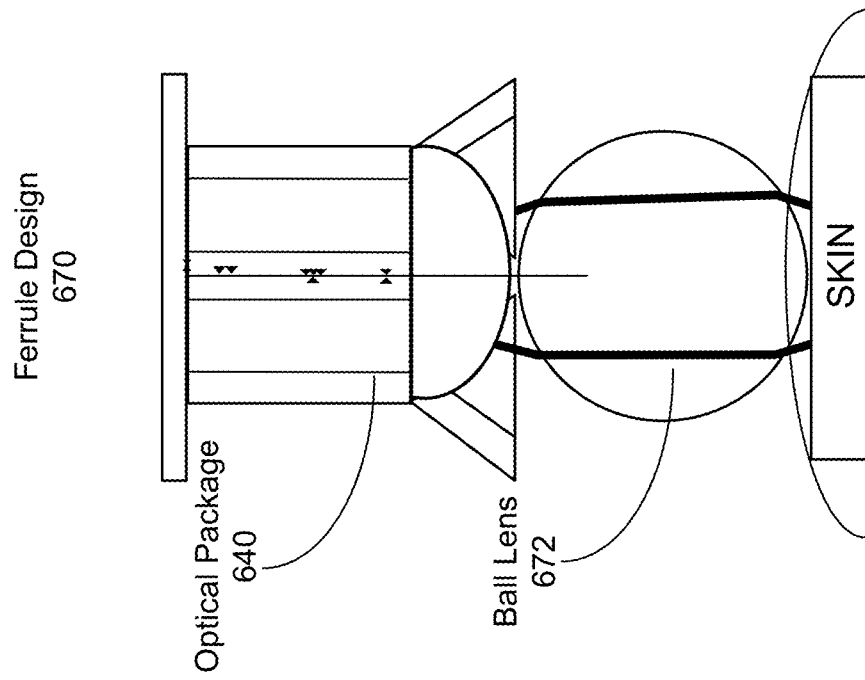
Figure 6F:
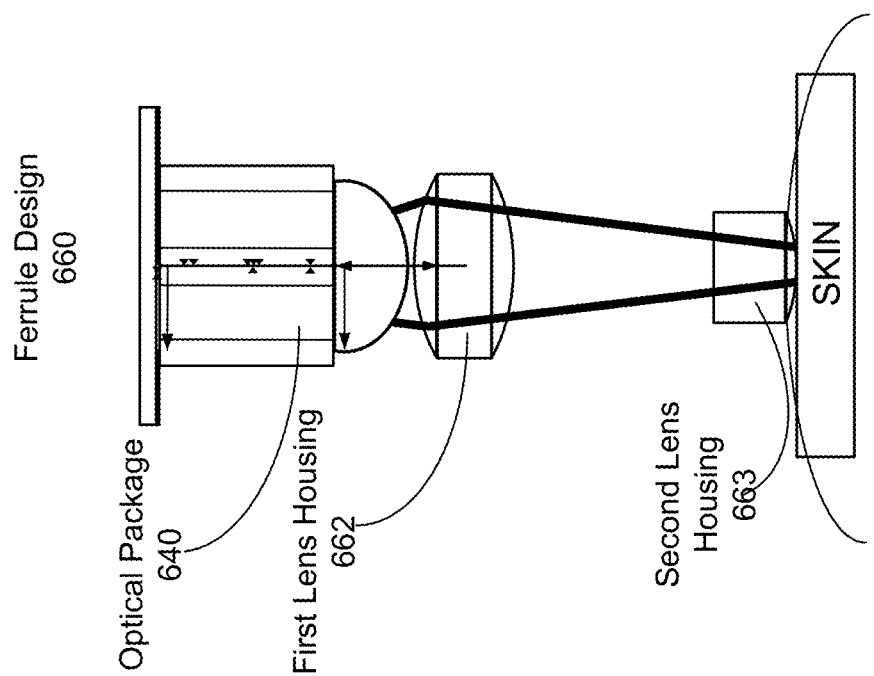

FIG. 6D illustrates an alternate ferrule design 650 in which the ferrule geometry is designed such that the light is focused when emitted from the optical package 640 (e.g., an emitter assembly) towards the head of a user or when detected by the optical package 640 (e.g., a detector assembly). FIG. 6E illustrates an alternate ferrule design 655 in which a stack of lenses, including first lens 657 and second lens 659, are installed within the ferrule body to focus the light emitted by the optical package 640 or detected by the optical package 640. Each of the first lens 657 and the second lens 659 may be integrated in the plastic casing of the ferrule to optimize an amount of light output at the tip of the ferrule. In some embodiments, a glass ball lens may be installed within the ferrule body. FIG. 6F illustrates a variation of the ferrule design 655 (illustrated in FIG. 6E) in which first lens is encased in a first lens housing 662 and the second lens is encased in a second lens housing 663. FIG. 6G illustrates an alternate ferrule design 670 in which a single ball lens 672 is used to direct light towards or away from the optical package 640. The ferrule design 670 may be used to reduce the overall form factor of an individual ferrule.

Figure 6I:
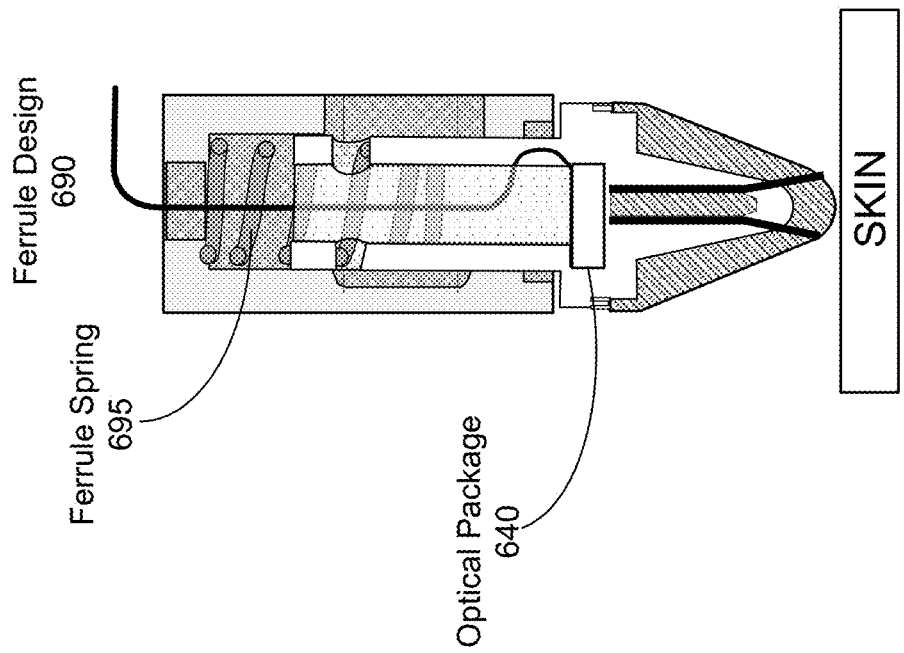
Figure 6H:
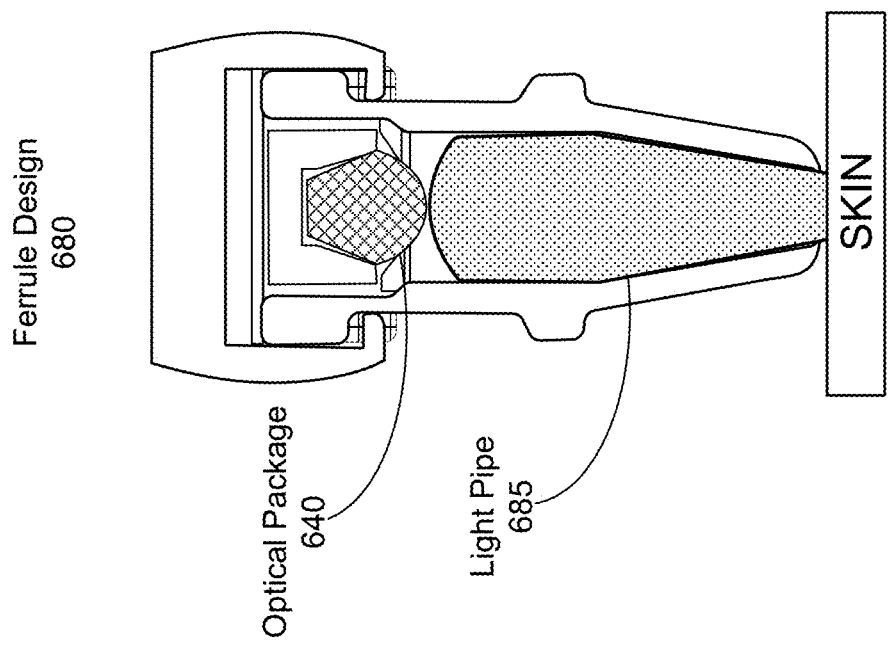

FIG. 6H illustrates an alternate ferrule design 680 involving a light pipe 685. Based on a change in index of refraction between the ferrule 680 and the surrounding air, the ferrule 680 guides light emitted by the optical assembly 640 towards the head of a user. The illustrated embodiment of FIG. 6H may be implemented in an emitter package to emit light towards the head of a user.

A ferrule, for example the ferrule designs illustrated in FIGS. 6C to 6H, may additionally be coated or metalized using a vapor coating a painting to prevent light leakage into or out of the ferrule.

Additionally, a ferrule of either an integrated detector assembly or an integrated emitter assembly may be designed to carry an electrical current. For example, the ferrule may be made using an electrically conductive material or may be coated with an electrically conductive material. As described herein, such an electrically conductive ferrule may be referred to as an optoelectrode. When worn by a user, a tip of the ferrule body is placed in contact with the skin of a user, for example the scalp of a user, and the opposite end of the ferrule is positioned in contact with an FPCA. In addition to directing optical signals towards a detector assembly, an electrically conductive ferrule, also carries electrical currents detected at the tip of the ferrule to circuitry on the FPCA, which measures electrical properties of the scalp. The measured properties include, but are not limited to, capacitance, impedance, or voltage at the location where the ferrule contacts skin of the user.

Each optoelectrode includes an optical interface at the tip of the optoelectrode for allowing an optical signal to travel from the scalp of a user into the ferrule. The optical signal then is able to travel through the ferrule (i.e., the core of the optoelectrode) to an optical package. Alternatively, the optical interface at the tip of the optoelectrode allows for a signal through the ferrule into the scalp of the user.

Furthermore, each optoelectrode includes an electrical interface at the tip of the optoelectrode to transfer electrical signals to or from the scalp of the user through the electrically conductive outer surface of the optoelectrode.

In some embodiments, such an optoelectrode may be implemented in a BCI module to measure electrical biological signals to aid in the decoding of optical biological signals, for example electroencephalography (EEG) signals. In other embodiments, optoelectrodes may be used to confirm ferrule contact with skin of a user and to confirm a quality optical transmission for both the emitter array and the detector array.

Figure 6K:
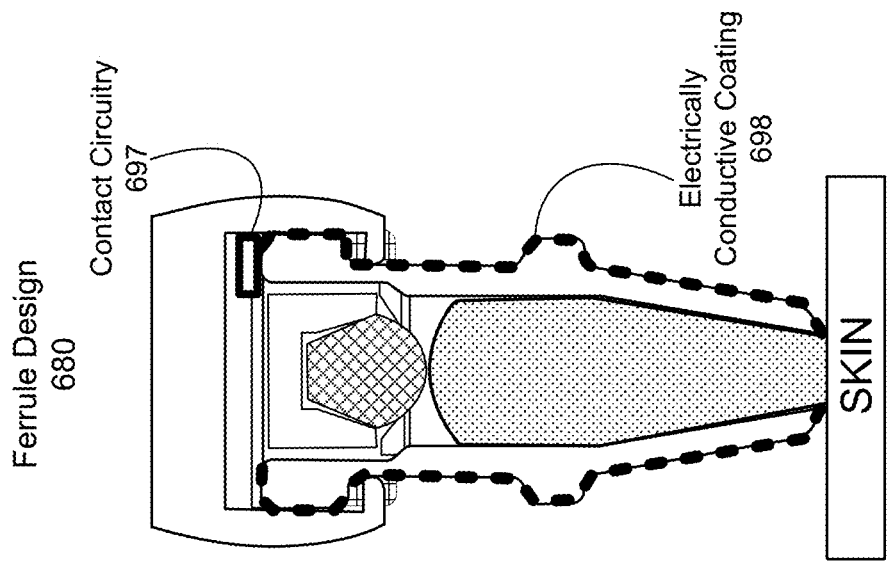
Figure 6J:
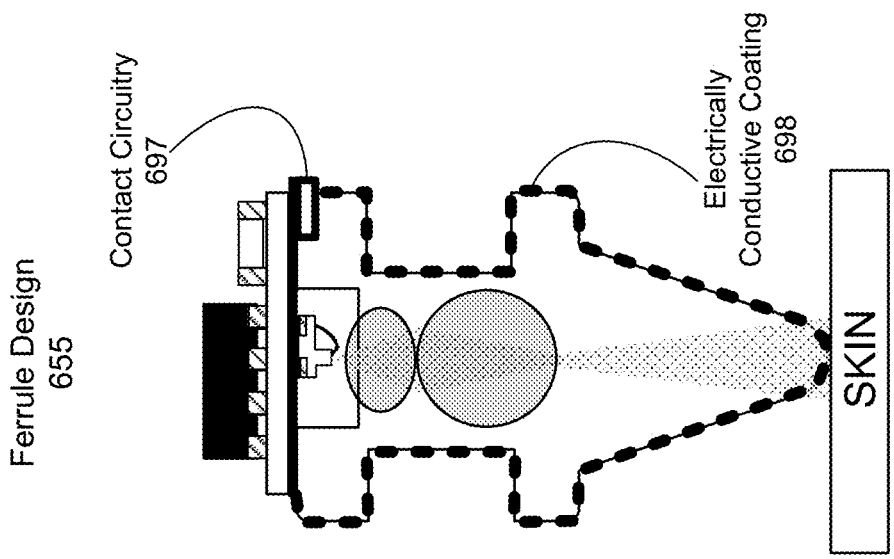

FIG. 6J illustrates an embodiment of an optoelectrode involving the ferrule design 655 described with reference to FIG. 6E. The ferrule is covered with an electrically conductive coating 698 the enable an electrical continuity between the scalp of a user and contact circuitry 697 on the FPCA. The contact circuitry 697 decodes and processes the electrical signal to measure the electrical properties described above. Similarly, FIG. 6K illustrates an embodiment of an optoelectrode involving the ferrule design 680 described with reference to FIG. 6H. The illustrated ferrule is covered in an electrically conductive coating 698 to communicate electrical signals to the contact circuitry 697 for processing. In addition to its conductive properties, the coating 698 may also function to block out light or prevent light leakage.

FIG. 6I illustrates an alternate ferrule design 690, which enables the ferrule to make greater contact with the skin than the previously discussed designs. The ferrule design 690 includes a ferrule spring 695. When the ferrule is not in contact with the skin (e.g., the scalp of a user) the spring is extended and ferrule design 690 is in a resting state. However, contact with the user's scalp results in a force applied to the tip of the ferrule and the compression of the ferrule spring 695. Compression of the ferrule spring 692 triggers a controller (not shown) to generate instructions for the optical assembly to emit light towards the user's head. In some embodiments, the compressive force applied to the ferrule spring 695 is provided by retainer 420 that is used to secure the BCI module 410 to the head of the user.

In some embodiments, the ferrule design 690 includes a cavity that houses the ferrule spring 695. Moreover, the cavity may house the optical package 640. The optical package 640 may be above the optical package 640. In some embodiments, the optical package 640 may be connected to the FPCA via a flexible cable or ribbon.

4.4 Flexible Printed Circuit Assembly

For a BCI module to accurately and most effectively detect signals, for example signals that characterize brain activity, the BCI module should conform to the geometry and structure of the heads of each individual user. When the BCI module is able to conform in such a way, the performance of each emitter ferrule assembly and detector ferrule assembly is increased. Accordingly, the BCI module comprises a flexible printed circuit assembly (FPCA) in combination with a stretchable ferrule retaining membrane to interconnect at least one emitter assembly and one detector assembly of the BCI module, or to connect the emitter assemblies and the detector assemblies to the controller circuitry 250.

Figure 7A:
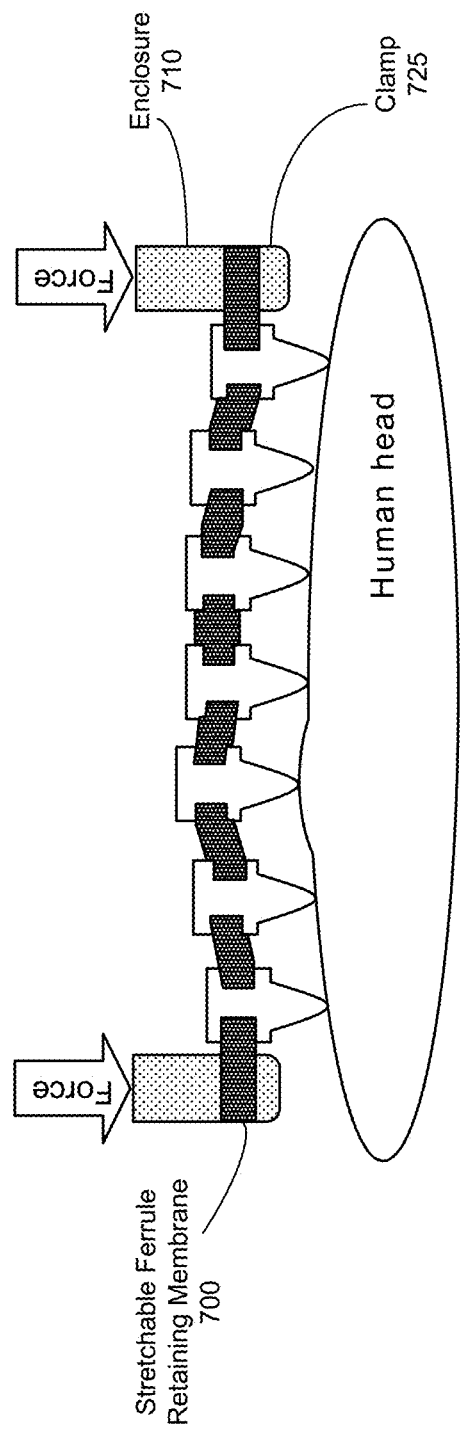
FIG. 7A is a side view of a flexible membrane configured to hold a plurality of ferrule assemblies in position, according to one embodiment.

To enable the BCI module to conform to a head of a user, each ferrule assembly is capable of moving independently to be able to conform to the shape of the head of the user. To enable the flexibility of the ferrule array, individual ferrules of the ferrule array are interconnected by a stretchable ferrule retaining membrane. FIG. 7A is a side view of a stretchable ferrule retaining membrane configured to hold a plurality of ferrule assemblies in position, according to one embodiment. The stretchable ferrule retaining membrane 700 is held in position by an enclosure 710, for example lower enclosure 275 or heatsink enclosure 245, on one face of the membrane 700 and a clamp 725 on the opposite face of the membrane 700. Between the membrane enclosure and the membrane retainer, the stretchable ferrule retaining membrane 700 retains a plurality of ferrules in position. The stretchable ferrule retaining membrane 700 enables conformity of the plurality of ferrules, both individually and collectively, to various head curvatures. When a force is applied to either end of the stretchable ferrule retaining membrane 700 or at any point along the membrane, each ferrule of the ferrule array conforms to the unique curvature of the head of the user. In some embodiments, the membrane 700 is designed out of poured or compressed molded rubber or silicone. In alternate embodiments, the membrane 700 may be designed using alternate materials or techniques that similarly enable the flexibility and conformity of the plurality of ferrules.

Figure 7B:
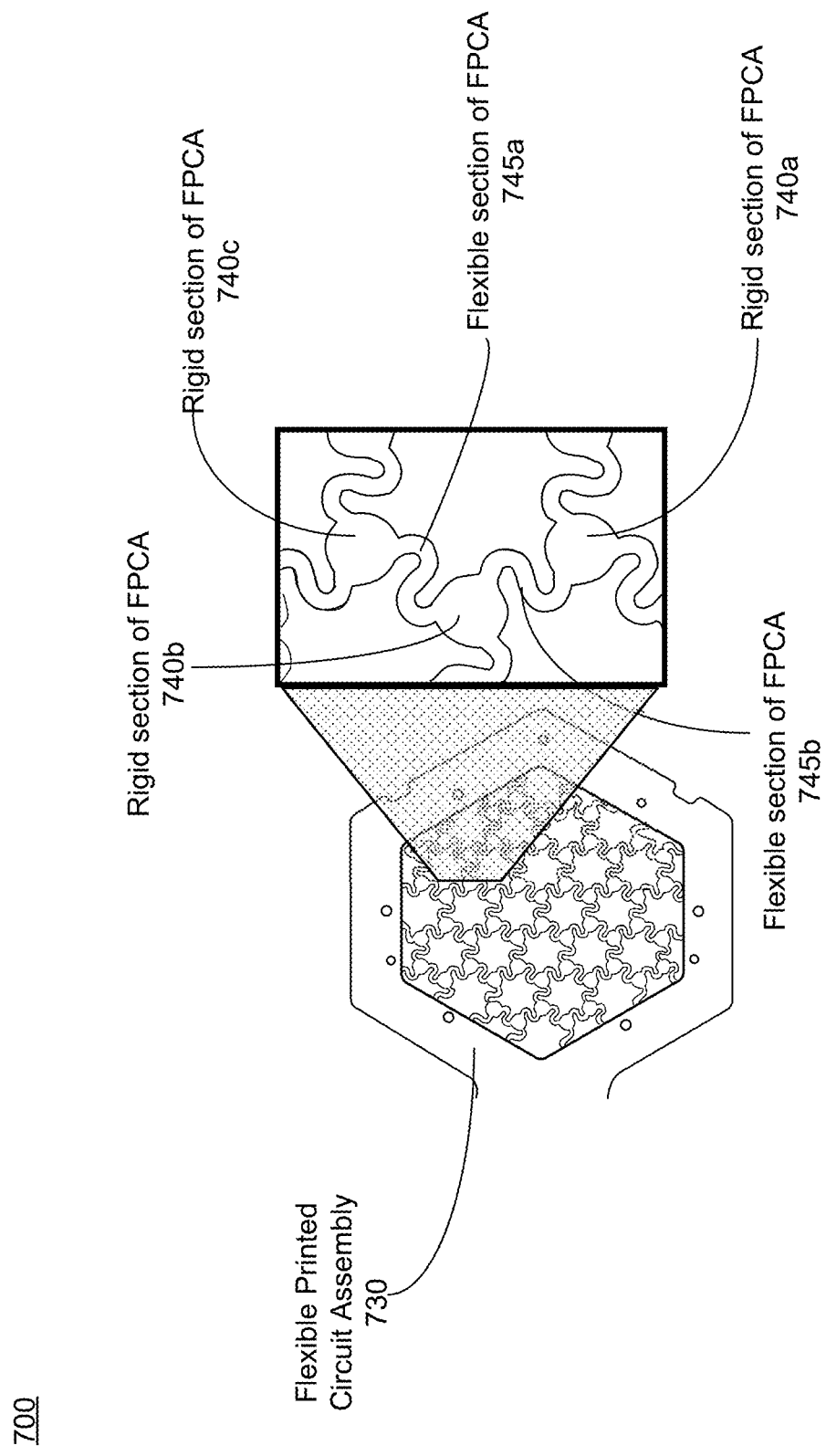
FIG. 7B-D illustrates connections between flexible sections of an FPCA and rigid sections of an FPCA, according to an embodiment.

Just as the stretchable ferrule retaining membrane 700 enables the conformity of each ferrule of a ferrule array to conform to unique curvatures, a BCI module comprises an FPCA is configured to enable the electrical connectivity of the electronic components of the BCI module (e.g., the emitter and detector packages and their respective controller) while also allowing flexibility of the electronic components. Electric components mounted to the FPCA are able to flex due to the stretchable properties of the FPCA, which are enabled by the geometries of flexible sections of the FPCA. FIG. 7B illustrates an FPCA with flexible sections connected to rigid sections, according to an embodiment. The FPCA 730 enables mechanical flexibility such that the optical packages and control components can conform to the curvature of a user's head. The FPCA 730 includes rigid sections 740a, 740b, and 740c. As described with reference to FIGS. 5A and 5B, an optical package (e.g., an emitter package or a detector package) and a controller are mounted on opposite sides of each rigid section 740. Each rigid section additionally has a ferrule mounted on the side of the optical package and a ferrule cap on the opposite side, forming an integrated ferrule assembly (i.e., the integrated emitter assembly 500 and integrated detector assembly 570). In alternate embodiments, both the controller and the optical assembly may be mounted to the same side of a rigid section 740.

The FPCA 730 enables the flexibility and conformity of the BCI module. However, once the FPCA has conformed to a user's head, each rigid section 740 independently holds the mounted ferrule assemblies (e.g., ferrule, optical package, and control components) in a fixed position, such that each ferrule assembly remains in continuous contact with the head of the user.

In one embodiment, emitter assemblies and detector assemblies are mounted to rigid sections 740 of the FPCA in a hexagonal formation. In other embodiments, the emitter and detector assemblies may be mounted to rigid sections in any other suitable geometric formation. Additionally, consistent with the description of FIGS. 4A and 4B, optical assemblies are mounted to rigid sections such that each rigid section with detector assemblies are surrounded by rigid sections with emitter assemblies. For example, if a detector assembly were mounted to rigid section 740*b*, emitter assemblies would be mounted to each of rigid section 740*a* and 740*c*.

In some embodiments, the rigid sections are made from a flexible, stretchable substrate and a rigid substrate mounted on the flexible substrate. For example, the flexible substrate may be a plastic or other polymer having conductive strips or traces and contact pads printed (or etched) onto it. The rigid substrate is then electrically connected to the flexible substrate to allow electrical signals to be transferred from the flexible substrate to the rigid substrate. In some embodiments, one or more components of the integrated ferrule assembly (e.g., an optical package or a control component) is mounted onto the rigid substrate. Moreover, in some embodiments, one or more components of the integrated ferrule assembly is mounted to the flexible substrate. For example, the control components may be mounted to the rigid substrate and the optical package may be mounted to the flexible substrate.

Each of the rigid sections 745 is interconnected to at least one neighboring rigid section by one or more flexible sections 745. In the illustrated embodiment of FIG. 7B, rigid sections 740*a* and 740*b* are interconnected by flexible section 745*a* and rigid sections 740*b* and 740*c* are interconnected by flexible section 745*b*. As described above with reference to FIGS. 5A and 5B, the flexible sections 745 enable each ferrule to flex and conform to the curvature of a user's head independent of other ferrules of the ferrule array.

The flexible sections 745 of the FPCA has a curved shape. In some embodiments, each flexible section 745 has an S shape with rigid sections 740 attached to each end of the S shaped flexible section. Although the curved shape of the flexible section 745 increases the length a trace travels to cross from a first rigid section to a second rigid section, the curved shape allows for increased ability of the FPCA to stretch and flexibility of electric components mounted to the FPCA. In addition to the illustrated and described designs of the flexible sections 745, any alternate design of flexible sections may be used to improve or enable the flexible sections, or the FPCA 730 as a whole, to stretch to conform to a head of a user. As such, the curved shape of the flexible sections 745 allows for a position of the ferrule assemblies to deviate from each other while maintaining physical and electrical connectivity between them.

Figure 7C:
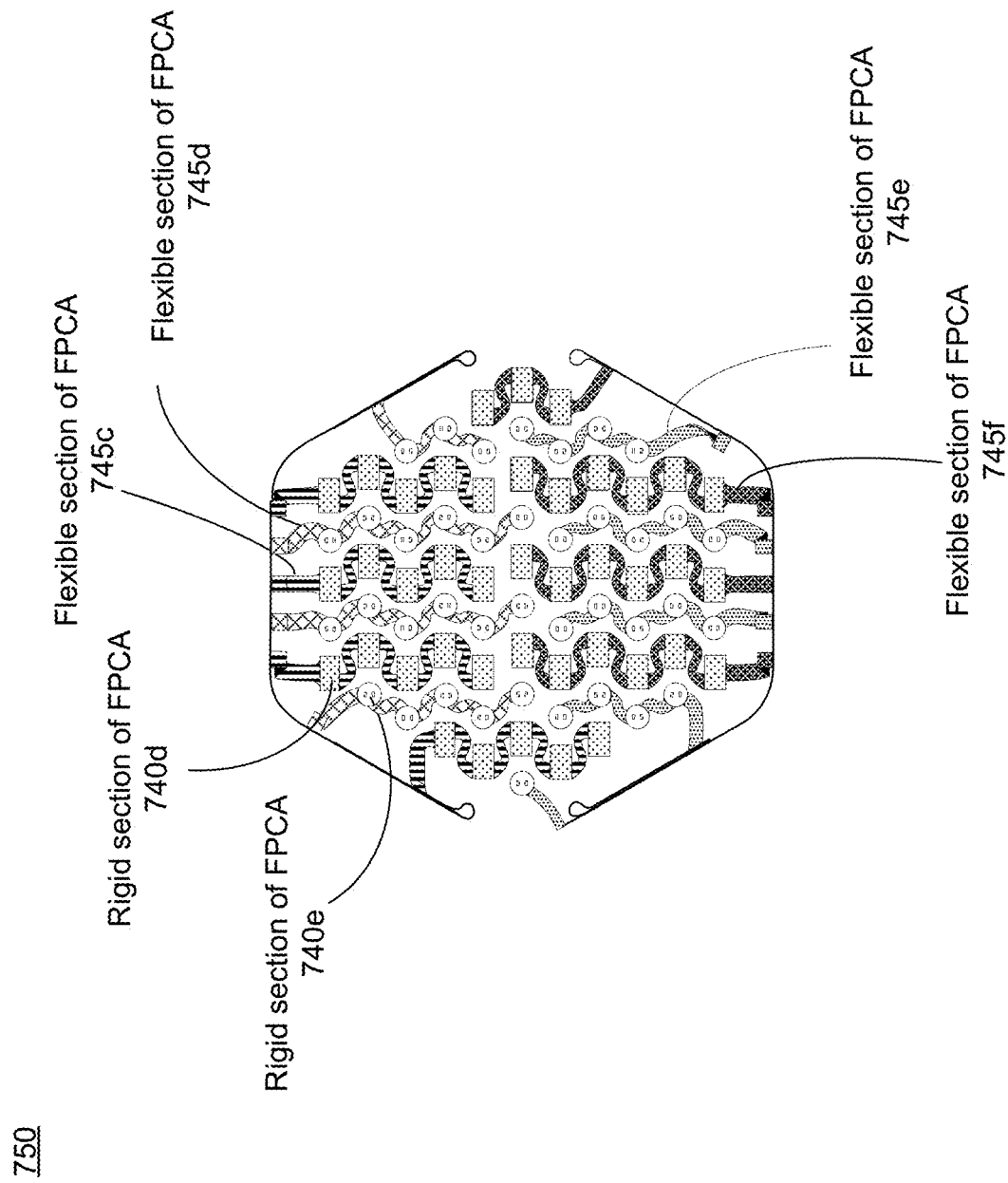
Figure 7D:
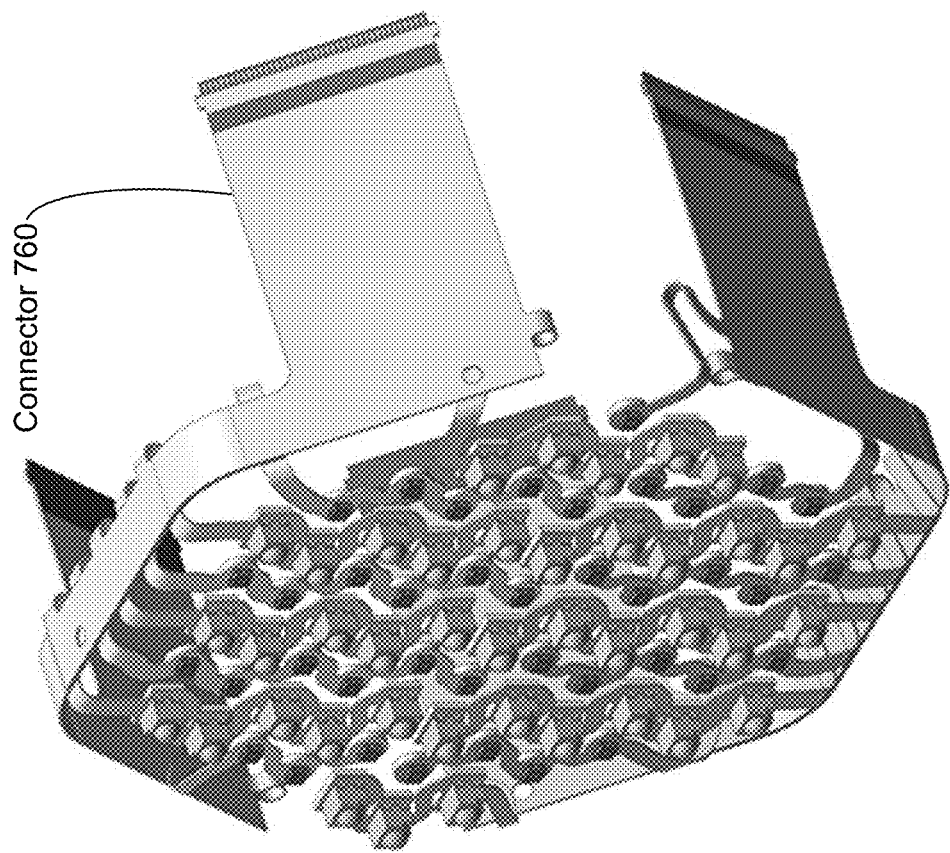
Figure 7D:
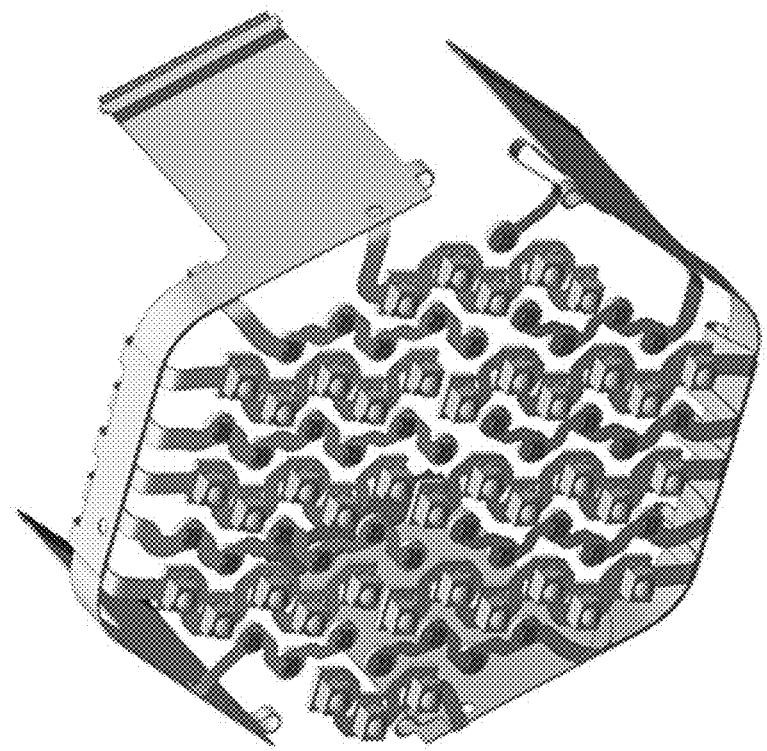

FIG. 7C illustrates an alternate embodiment of an FPCA with flexible sections connected to rigid sections, according to an embodiment. The illustrated FPCA 750 includes rigid sections 740 for mounting emitters, detectors, control circuits, and additional sensors. In the illustrated embodiment of FIG. 7C, each rigid section of the FPCA may be designed with unique geometries depending on the circuit elements mounted on the rigid section. For example, rigid section 740*d* and rigid section 740*e* are designed with unique geometries to mount different optical elements or circuit components. The flexible sections of the FPCA are designed with geometries that enable each rigid section to stretch and flex relative to any neighboring rigid sections. Flexible sections, for example flexible sections 745*c*, 745*d*, 745*e*, and 745*f*, may be designed unique geometries to enable each rigid section to stretch and flex to various degrees or orientations. Additionally, each flexible section may be designed as part of a flexible branch in a set of multiple interwoven flexible branches that lead back to a common printed circuit board. The rigid sections 740 may then be mounted on specific sections of the stretchable branches. FIG. 7D illustrates isometric views of the FPCA 750, according to an embodiment.

In some embodiments, the flexible branches of the FPCA are formed by cutting a flexible printed circuit board (PCB). Each of the flexible branches may then be folded to a desired position. In some embodiments, the FPCA includes multiple flexible PCBs that are interwoven together. For example, the embodiment of FIG. 7D includes four flexible PCBs, two flexible PCBs to form flexible sections for detectors and two flexible PCBs to form flexible sections for emitters. Each flexible PCB may include a connector 760 at one end to allow the FPCA to connect to a controller board that controls the operation of the emitters and detectors mounted on the FPCA. The flexible branches of the FPCA may be designed stretch and flex as described above with reference to the flexible sections 745.

Each of the flexible branches include metal traces for routing an electrical signal from the connector 760 to a rigid section 740 mounted on the flexible branch. In some embodiments, each branch includes a separate metal trace (or set of metal traces) for each of the rigid sections mounted on the flexible branch. In other embodiments, each flexible branch includes a single set of metal traces that are shared be every (or a subset) of rigid sections mounted on the flexible branch. For example, the set of wires may be a bus that can be multiplexed to allow signals to be addressed to individual rigid sections.

Additionally, in some embodiments, each flexible branch has a corresponding set of terminals in the connector 760. As such, a controller circuit connected to the connector 760 is able to send control signals and receive measurement signals from each of the stretchable branches independently. In other embodiments, each flexible branch is coupled to one or more buses. In this embodiment, the signals corresponding to each individual stretchable branch may be multiplexed to allow a controller circuit to communicate with emitters or detectors mounted on each flexible branch independently.

Figure 7E:
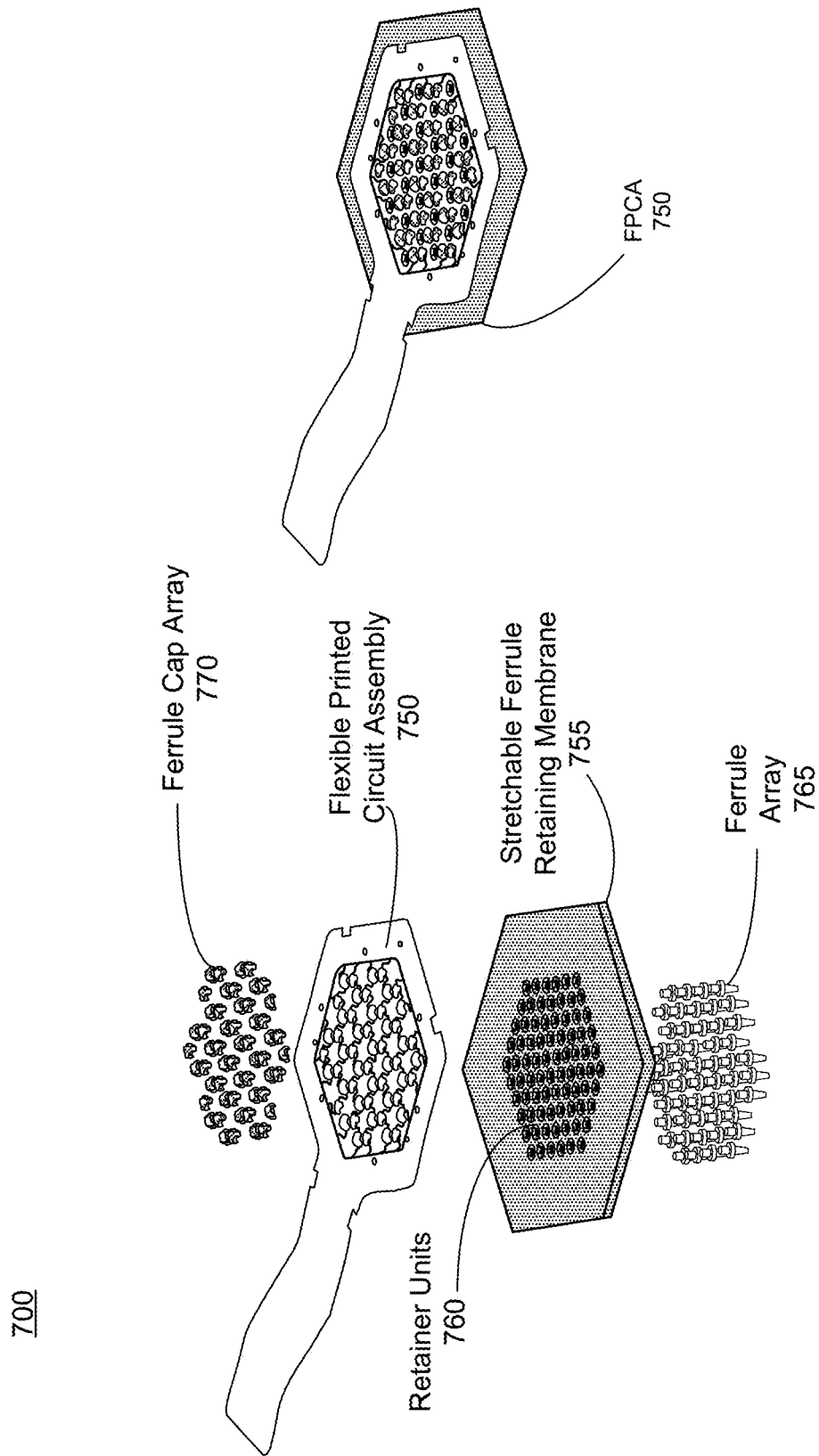
FIG. 7E is an isometric view of components of an FPCA, according to an embodiment.

FIG. 7E is an isometric view of the FPCA, ferrule array, ferrule caps, and stretchable ferrule retaining membrane, according to an embodiment. The stretchable ferrule retaining membrane 755 retains each ferrule of the ferrule array 765 in a fixed position. As illustrated, the membrane 755 includes a plurality of retainer units 760, each of which can hold a single ferrule of the ferrule array 765. The FPCA 750 is overlaid onto the stretchable ferrule retaining membrane 755, such that rigid sections of the FPCA 750 align with at least a subset of retainer units of the stretchable ferrule retaining membrane 755. Once aligned and overlaid, optical packages mounted to each rigid section are inserted into a cavity of a ferrule retained by the corresponding retainer unit. The ferrules are secured to the FPCA 750 by ferrule caps of ferrule cap array 770, such that a rigid section of the FPCA together with the optical package and controller are encased between a ferrule and a ferrule cap.

4.5 Signal Generation Methods Using Emitter and Detector Arrays

Figure 8:
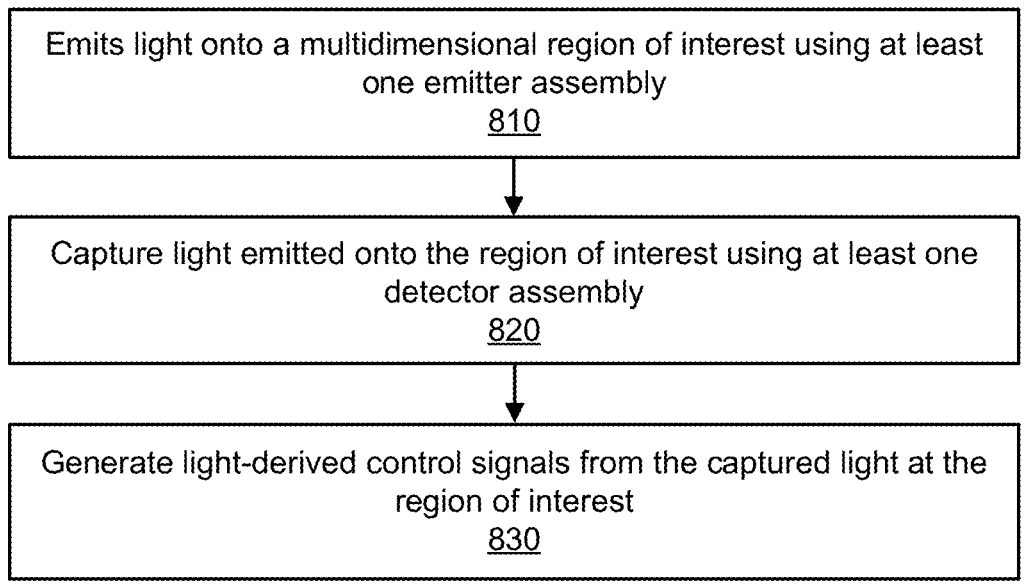
FIG. 8 is a flow chart illustrating a method for generating and processing optical signals, according to an embodiment.

FIG. 8 is a flow chart illustrating a method for generating and processing optical signals, according to an embodiment. The method 800 functions to enable decoding of optical signal-derived data from a region of interest, for example using high dynamic range sensors of a detector array and individually addressable light emitting components of an emitter array in a compact BCI module.

As shown in FIG. 8, an emitter array, through individual emitter assemblies, emits 810 light onto a multidimensional region of interest, which functions to provide controlled transmission of light that can be received by a sensor for characterization of the region of interest. The light transmitted from the multidimensional region of interest can include light in the non-visible spectrum and/or light in the visible spectrum, can include a single wavelength of light or multiple wavelengths of light, can include naturally encoded information (e.g., due to physiologically induced phenomena), and/or can include synthetically encoded information (e.g., due to polarization or other light manipulating optics positioned along a light transmission pathway). The transmitted light can be associated with any energy associated factors (e.g., power, duration of transmission, intensity), waveform factors (e.g., pulsed, non-pulsed, waveform shape), temporal factors (e.g., frequency of signal transmission), and/or any other suitable factors.

In relation to the interface described above, the multidimensional region of interest is a head-region of the user, where noninvasively-acquired light signals can be used to decode brain activity of the user through the head region. The head region can include one or more of: a frontal region, a parietal region, a temporal region, an occipital region, an auricular region, an orbital region, a nasal region, or an infraorbital region. Additionally, or alternatively, the head region can include other cranial or facial regions including one or more of: an oral region, a parotid region, a buccal region, or any other suitable region of the head of the user. In alternative embodiments, the multidimensional region of interest can be associated with another anatomical region of the user. Additionally, or alternatively, the multidimensional region can be associated with a surface or volume of material of another object.

Individual detector assemblies of a detector array detect and capture 820 light emitted onto the region of interest. The captured light is derived from light that originated at the set of emitter assemblies and interacted with the multidimensional region of interest (e.g., the head of the user). The captured light can thus be associated with light sourced from individually addressable emitter assemblies, where light output from the emitter assemblies can be timed according to scanning of the detector according to methods described below. The detector assemblies can additionally or alternatively capture light derived from ambient light from the environment of the user, where the ambient light has interacted with the multidimensional region of interest. Light detections through the set of detector assembly can, however, come from any other suitable source.

After light is captured 820 by detector assemblies, a controller associated with the detector array generates 830 light-derived signals for characterization of the region of interest. Alternatively, the captured light may be received by a controller associated with an individual detector package of the array. The scanning operation(s) of the controller provide fast readout, in order to facilitate rapid processing and decoding of information (e.g., neural stream data) derived from incident light on the illuminated regions of the head.

In generating 830 light-derived signals, the controller reads electrical signals produced from the reflected light detected by the detector array. The controller reads the detected light reflections sequentially in order to produce fast readout speeds. Furthermore, the controller reads the detected reflections in a linear manner. However, in alternate embodiments, the controller can read detected reflects in any other suitable path. The scanning operation can read full frames of signals of reflected light and/or can read less than full frames of signals (e.g., a central line of signals along the scan path). The scanning operation can be specified with parameters related to speed (e.g., in terms of frame rate), power consumption, or any other suitable parameter.

As described above, the detector array, with the controller, can be configured to coordinate scanning operation with light output through individually addressable light emitters (e.g., light emitters of the VCSEL array, LED light emitters, etc.). As such, to generate 830 the light-derived signals, a portion (e.g., a first subset) of emitter assemblies are activated and the detector array scans the illuminated region of the head in coordination with activation of the portion of light emitters. Then, a second portion (e.g., a subset the same as or different from the first subset) of emitter assemblies are activated and the detector array scans the illuminated region of the head in coordination with activation of the second portion of light emitters. In this example, portions of emitter assemblies can be activated in a manner to minimize crosstalk/interference due to light emission, or to serve any other suitable purpose. However, the first portion and the second portion of emitter assemblies activated can be associated with targeting different portions of the region of interest (and not necessarily to minimize crosstalk/interference). However, in alternative embodiments, coordination of timing between light emission and scanning by the detector array can be conducted in any other suitable manner.

Generating light-derived signals can facilitate extraction of features from illuminated regions of a user's head, where features can be extracted from illuminated central regions and/or unilluminated edge regions of the grouped pixel units in order to increase dynamic range of the sensor outputs by several orders of magnitude relative to unsaturated sensor configurations. Features related to saturated portions can include positions of boundaries between a saturated central region and unsaturated edge regions (indicative of total power), diameter of a saturated central region, projected area of a saturated central region, or any other suitable shape-related features associated with the saturated central region. Features related to unsaturated edge regions can include positions of boundaries between unsaturated edge regions, slope related features (e.g., rates of decay) of a heel portion of an unsaturated edge region, features related to integrated areas under an intensity curve corresponding to unsaturated edge regions, or any other suitable shape-related features associated with the unsaturated edge region. While features associated with intensity are described above, features that can be derived from the generated light signals can include features of any other suitable light-related parameter. Furthermore, in relation to the region of interest being at a head region of the user, the features of interest can be decoded to distinguish different types of brain activity of the user, which can be used as control inputs for controlling operation states of other systems (e.g., virtual assistants, interactions with an online social network, smart home devices, etc.). As described in more detail in relation to FIGS. 10A-10E below.

4.6 System—Additional Sensors

As shown in FIG. 1A, the BCI system can include additional sensors 140 for detecting user behaviors and/or other biometric signals that can supplemental data.

Figure 9A:
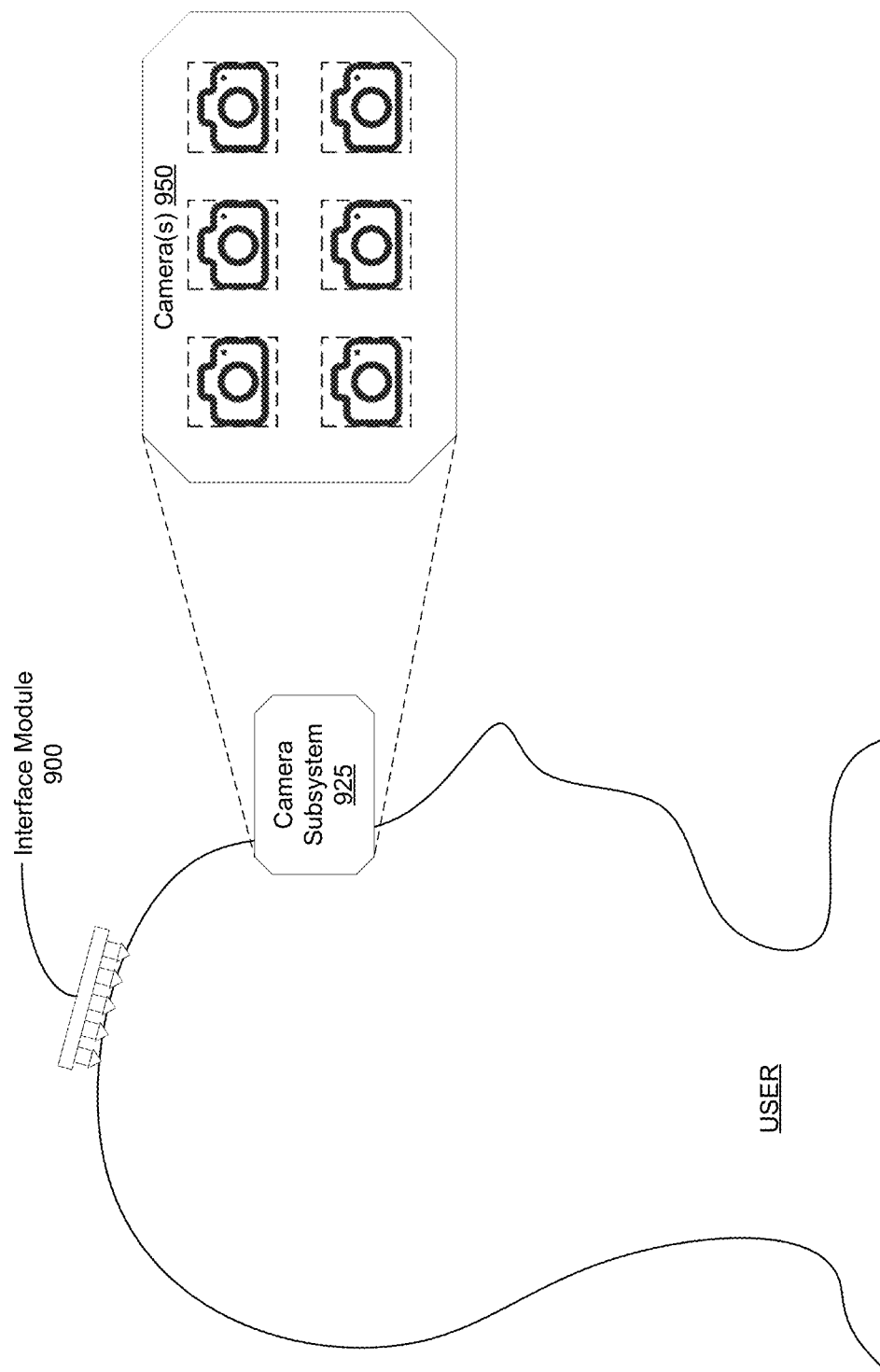
FIG. 9A illustrates a schematic of a camera subsystem, according to an embodiment.
Figure 9B:
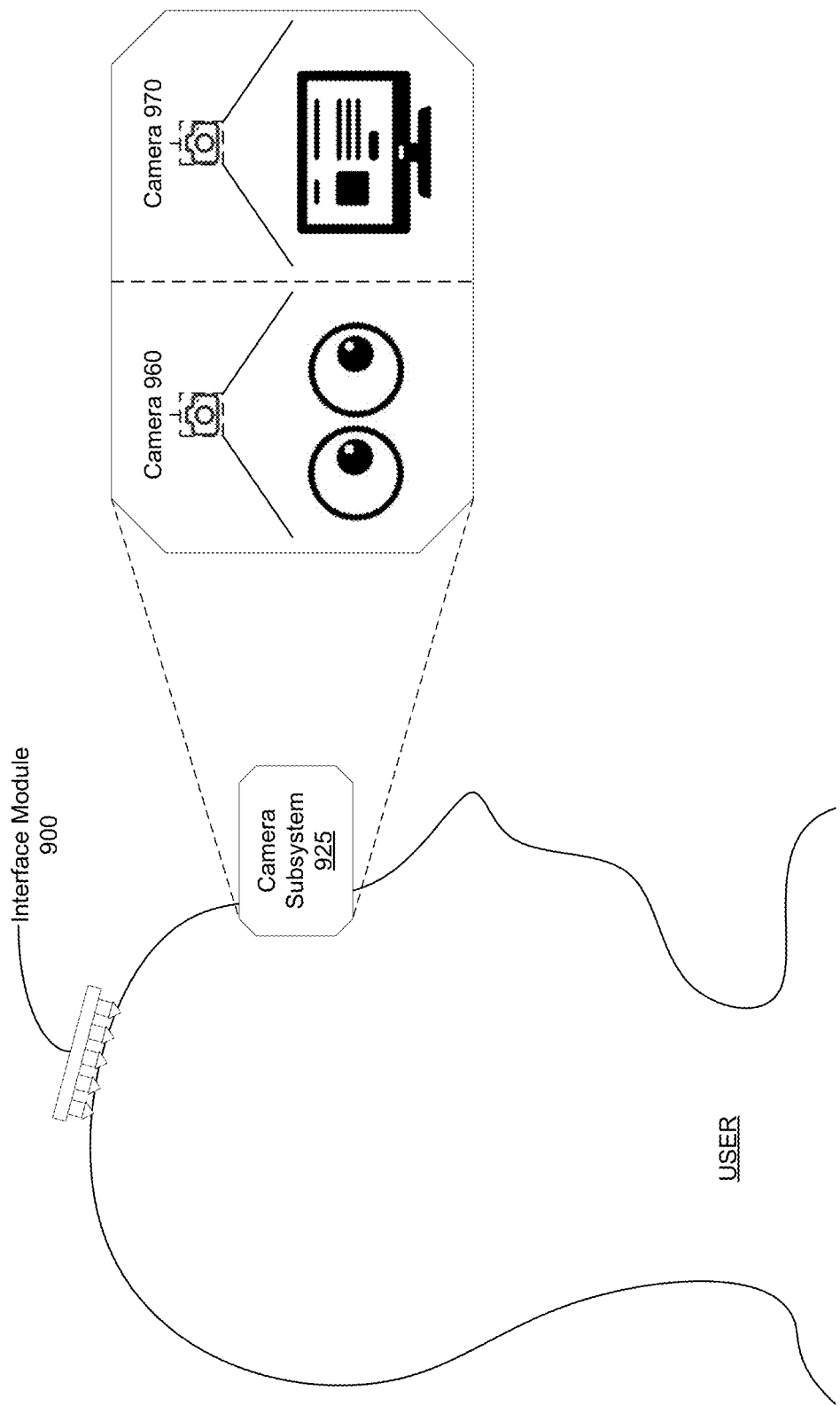
FIG. 9B illustrates a schematic of a camera subsystem, according to an embodiment.
Figure 10A:
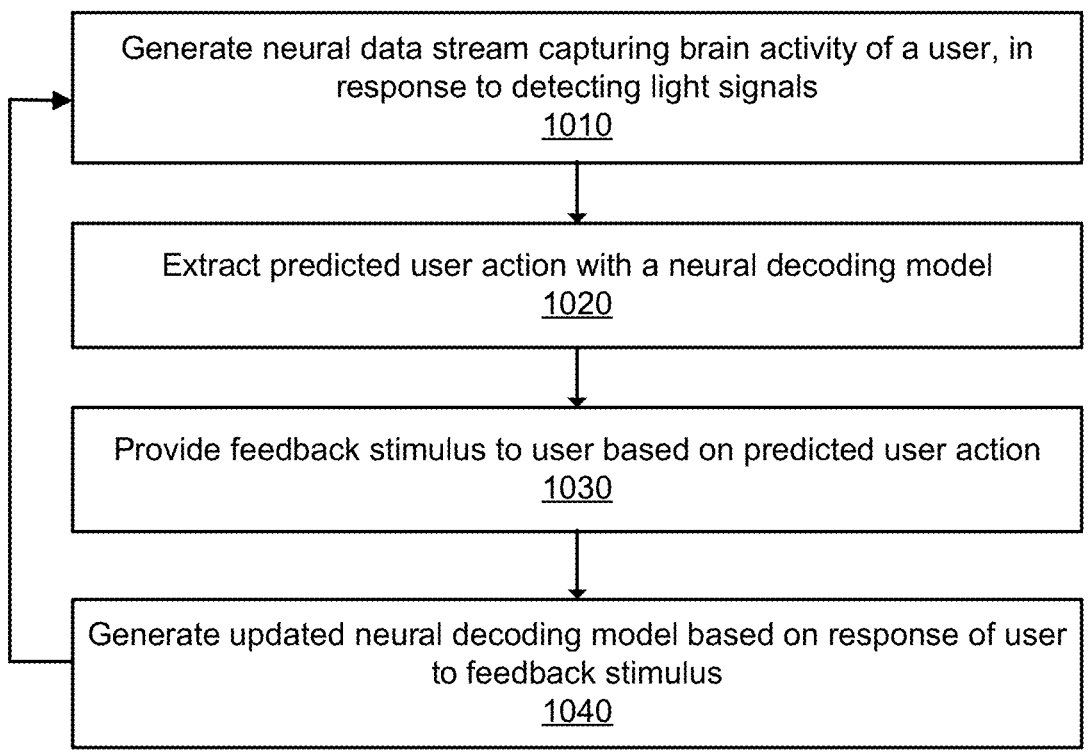
FIG. 10A is a flow chart illustrating a method for neural decoding, according to an embodiment.
Figure 10B:
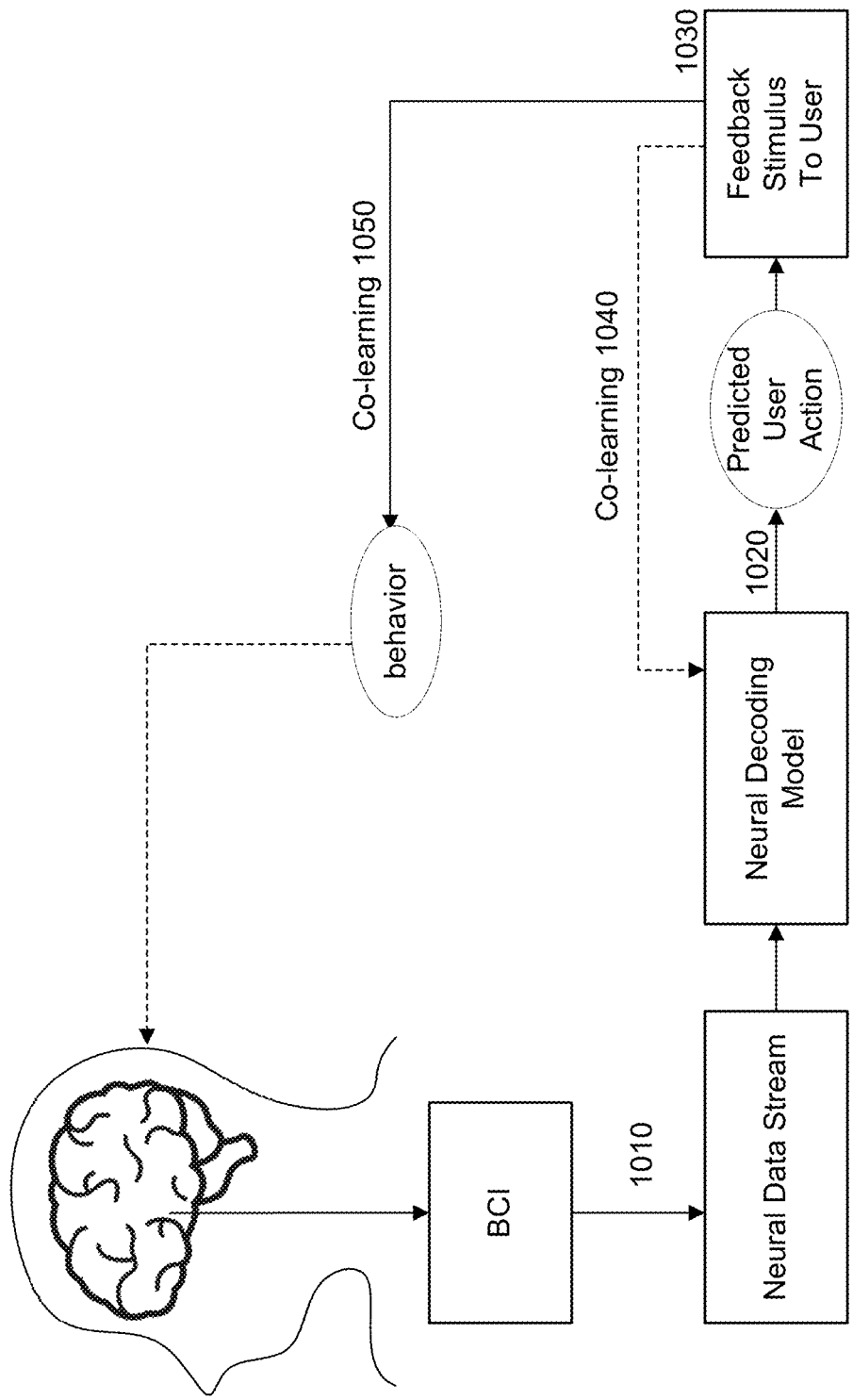
FIG. 10B is a flow diagram for an embodiment of the method for neural decoding shown in FIG. 10A, according to an embodiment.

FIG. 9A illustrates a schematic of a camera subsystem 925, according to an embodiment, and FIG. 10B illustrates a schematic of the camera subsystem 925 shown in FIG. 9A.

As shown in FIG. 10, the additional sensors can include one or more cameras 950 of a camera subsystem 925, which function to generate image data of the user and/or of an environment of the user. The cameras 925 utilize light of the visible spectrum, but can additionally or alternatively include sensors that utilize any other portion of the electromagnetic spectrum (e.g., infrared spectrum). The camera subsystem 925 can use image sensors of the camera(s) 950 to capture image data and/or video data. In relation to image data and video data, the camera subsystem 925 can be configured to capture data with sufficiently high resolution to capture features of interest of the user (e.g., pupil position and orientation, facial features, body movements, etc.) and/or of the environment of the user (e.g., states of objects in the environment of the user), where applications of user tracking and environmental tracking are described in more detail below.

In relation to the wearable interface 110 described above, the camera(s) 950 of the camera subsystem 925 can be coupled to the wearable interface (and electronics subsystem 1050) shown in FIGS. 10A and 10B, in a manner that orients the camera(s) with a field of view capturing the face (or a portion of the face) of the user, and/or with a field of view capturing an environment of the user (e.g., from a point of view of the user). As such, the camera subsystem 925 can include a first camera 960 coupled to (e.g., mounted to, electromechanically coupled to, etc.) a portion of the wearable interface and in an inward-facing orientation to provide a field of view capturing the face of the user, in order to generate eye tracking data (e.g., in relation to coordinates of objects the user looks at, in relation to swell time) of the user and/or facial expressions of the user. The camera subsystem 925 can also include a second camera 970 coupled to (e.g., mounted to, electromechanically coupled to, etc.) a portion of the wearable interface and in an outward-facing orientation to provide a field of view capturing the environment of the user, in order to generate image data of objects or environments with which the user is interacting. The camera subsystem 925 can, however, have more than two cameras coupled to the wearable interface or other portions of the system in another orientation. Additionally, or alternatively, the camera(s) can be fixed in position, or can be actuated to adjust field of view.

As indicated above, the camera subsystem 925 can cooperate with other portions of the system described above, in applications where capturing interactions of the user with the environment of the user can be combined with decoded brain activity of the user in a useful manner. In one such application, the system can monitor, by way of cameras 950 of the camera subsystem 925, objects that the user is interacting with in his/her environment by generating and analyzing images of eye motion of the user, head motion of the user, gaze of the user, and/or line-of-sight to objects in the user's environment, decode an intention of the user from brain activity of the user acquired through the detector array described above, and apply the intention as an input to control an operational state of the object. Examples of objects can include electronic content provided at a display (e.g., of a computer, of a wearable device, of an artificial reality system, of a virtual reality system, of an augmented reality system, etc.), electronic content provided at an audio output device, electronic content provided at a haptic feedback device, connected devices (e.g., temperature control devices, light control devices, speakers, etc.), or other objects. Examples of intentions can include desired adjustments to operational states of devices (e.g., turn off device, turn on device, adjust device brightness, adjust device output volume, etc.), desired interactions with electronically-provided content (e.g., select object, select menu item, navigate to another web page, scroll up, scroll down, close window, etc.), desired interactions with a virtual assistant, or any other intentions.

As such, in one specific example, the camera subsystem 925, in combination with other system outputs, can cooperate to determine that the user is looking at a particular connected light in the user's bedroom, decode a brain activity signal that indicates that the user wants to dim the light, and generate control instructions for dimming the light, all without the user speaking a command or adjusting dimness of the light using a physically-manipulated controller. In another specific example, the camera subsystem 925, in combination with other system outputs, can cooperate to determine that the user is looking at a selectable button for purchasing an item within an online marketplace, decode a brain activity signal that indicates that the user wants to "click the button", and generate control instructions for selecting the button to purchase the item, all without the user speaking a command or physically clicking the button (e.g., with a mouse).

In relation to the additional sensors 140a shown in FIG. 1A, the system can additionally or alternatively include other sensors and/or biometric sensors for sensing aspects of the user, the user's physiology, and/or the environment of the user. Other sensors can include audio sensors (e.g., microphones), motion/orientation sensors (e.g., accelerometers, gyroscopes, inertial measurement units, etc.), respiration sensors (e.g., plethysmography sensors), cardiovascular sensors (e.g., electrical signal-based cardiovascular sensors, radar-based cardiovascular sensors, force-based cardiovascular sensors, etc.), temperature sensors for monitoring environmental temperature (e.g., ambient temperature) and/or body temperature of the user, other brain activity sensors (e.g., electroencephalography sensors), other electrophysiology sensors (e.g., skin conductance sensors), and/or any other suitable sensors.

Outputs of the additional sensors 140a can be processed with outputs of other system components described above, in order to improve applications where co-processing brain activity information with other sensor-derived information would be beneficial.

4.6 System—Other Electronics

The system can include additional electronics coupled to one or more of the embodiments of the emitter, detector array, additional sensors, network, and/or wearable interface, as described above.

For instance, the system can include a power component that provides power and/or manages power provision to one or more other system components. The power component can include a battery (e.g., rechargeable battery, non-rechargeable battery) electrically coupled to a power management system that maintains desired circuit voltages and/or current draw appropriate for different system components. The power component can be retained within a housing (e.g., enclosures 245 and 255 of the BCI module 200) associated with the wearable interface and coupled to the emitter array and/or the detector array. As described in relation to other system components below, the housing can house one or more of: the emitter array, the detector array, a power component, a computing component, a data link, and additional sensors. The housing can also house at least a portion of the BCI interface that is head-mountable for positioning signal transmission components at the head region of a user. The housing can be head-mounted or can be coupled to the user in another manner. The housing can be composed of a polymer material and/or any other suitable materials.

As shown in FIG. 1A, the system can also include a computing device 160 that functions to coordinate light transmission from the emitter array and/or operation states of the detector array (e.g., in relation to emission from the emitter array). The computing component can thus include architecture storing instructions in non-transitory computer readable media for implementing portions of methods described, controlling operation states of the emitter array, the detector array, and/or additional sensors, monitoring states of components coupled to the computing component, storing data in memory, coordinating data transfer (e.g., in relation to the data link described below), and/or performing any other suitable computing function of the system. The computing component can additionally or alternatively include signal conditioning elements (e.g., amplifiers, filters, analog-to-digital converters, digital-to-analog converters, etc.) for processing signal outputs of sensors of the system.

The system can also include a data link coupled to the computing device, for handling data transfer between electronics of the wearable system components and the network 170a. The data link can provide a wired and/or wireless (e.g., WiFi, Bluetooth LE, etc.) interface with the network or other external systems.

5. Method—Neural Decoding Process with Co-Learning

FIG. 10A illustrates a flow chart of a method 1000 for neural decoding, according to an embodiment. FIG. 10B illustrates a flow diagram for an embodiment of the method for neural decoding shown in FIG. 10A, according to an embodiment. As shown in FIGS. 10A and 10B, the system (e.g., light transmission, light detection, and computing components) generates 1010 a neural data stream capturing brain activity user in response to detecting a set of light signals from a head region of a user as the user interacts with an object in an environment. The system extracts 1020 a predicted user action upon processing the neural data stream with a neural decoding model, where the predicted user action can be actual (e.g., actual speech) or imagined (e.g., thought), as described in more detail below. The system then provides 1030 a feedback stimulus to the user based upon the predicted user action, and generates an updated neural decoding model based upon a response of the user to the feedback stimulus 1040. The system also implements one or more co-learning processes 1040, 1050 for improvement of the neural decoding model and/or behavior of the user. As such, the method 1000 can provide a closed loop process whereby the neural decoding model is updated and trained as the user interacts with content or other stimuli, and provides additional light-derived signals that capture brain activity.

The method 1000 functions to rapidly (e.g., in real time or near real time) decode light-derived signals to extract predicted user actions or intents (e.g., commands) in relation to interactions with objects (e.g., virtual objects, physical objects), such that the user can manipulate the objects or otherwise receive assistance without manually interacting with an input device (e.g., touch input device, audio input device, etc.). The method 1000 thus provides a neural decoding process with the neural stream signal as an input, and provides feedback to the user, where the feedback is used to train the neural decoding algorithm and user behavior. The neural signals can be blood oxygenation level dependent (BOLD) signals associated with activation of different articulators of the motor cortex, and signals can characterize both actual and imagined motor cortex-related behaviors. With training of the decoding algorithm, rapid calibration of the system for new users can additionally be achieved.

5.1 Method—Generating Data

As shown in FIGS. 10A and 10B, the BCI system (e.g., light transmission, light detection, and computing components) generates 1010 a neural data stream capturing brain activity of the user as the user interacts with an object, which functions to generate source data that can be processed with the neural decoding model to decode cognition through a non-traditional method. As noted above, the neural data stream is derived from input light signals that are provided to the user's head and output light signals that are captured after passing through the user's head, where the output signals carry information about the level of oxygen present in blood of the user, associated with different regions. As such, the signals associated with the neural data stream are a type of blood oxygen-level dependent (BOLD) signal that carries hemodynamic response information. In use, signals generated can be evaluated for reliability, such that only reliable signals are passed by the controller through downstream processing steps to generate predicted user actions. Reliability can be evaluated based upon consistency in signal characteristics (e.g., variances around a mean signal characteristic).

As described above in relation to the detector array, in generating the neural data stream, the BCI system can transform input signals from a detector-associated region of the head to a brain region-associated space (e.g., in relation to brain regions associated with the input signals). Also described above in relation to embodiments of the detector array, signals of the neural data stream that are derived from light emitted at distinct head regions, where features can be extracted from saturated central regions and/or unsaturated edge regions. The signals derived from saturated portions can include information related to positions of boundaries between a saturated central region and unsaturated edge regions (indicative of total power), diameter of a saturated central region, projected area of a saturated central region, or any other suitable shape-related features associated with the saturated central region. Features related to unsaturated edge regions can include positions of boundaries between unsaturated edge regions of the, slope related features (e.g., rates of decay) of a heel portion of an unsaturated edge region, features related to integrated areas under an intensity curve corresponding to unsaturated edge regions, or any other suitable shape-related features associated with the unsaturated edge region. While signal characteristics associated with intensity are described above, signal characteristics that can be derived from the generated light signals can include features of any other suitable light-related parameter.

Also described above in relation to the detector array, the system can generate signals of the neural data stream associated with multiple light exposure levels (e.g., short and long exposure levels), different light power settings (e.g., a low power setting, a high power setting), and/or different light parameter settings.

In relation to the detector array described above, the neural data stream includes data from separate head regions (e.g., separate head regions associated with a single cortex, separate head regions associated with multiple cortices) of the user. In one embodiment, the neural data stream includes light data from different head regions, where signals from the different head regions map to a set of motor cortex articulators associated with articulation of different speech components. Articulation can be actual or imagined, such that the signals can carry information associated with actual or imagined speech. Furthermore, with repeated iterations of the method 1400, the controller can generate a template that refines mapping between the detector array components and specific brain anatomy of the user(s) associated with the method 1000. Over time, aggregation and processing of large amounts of data from the user(s) can be used to provide rapid calibration of system components and system response for the user(s) and/or new users.

Figure 10C:
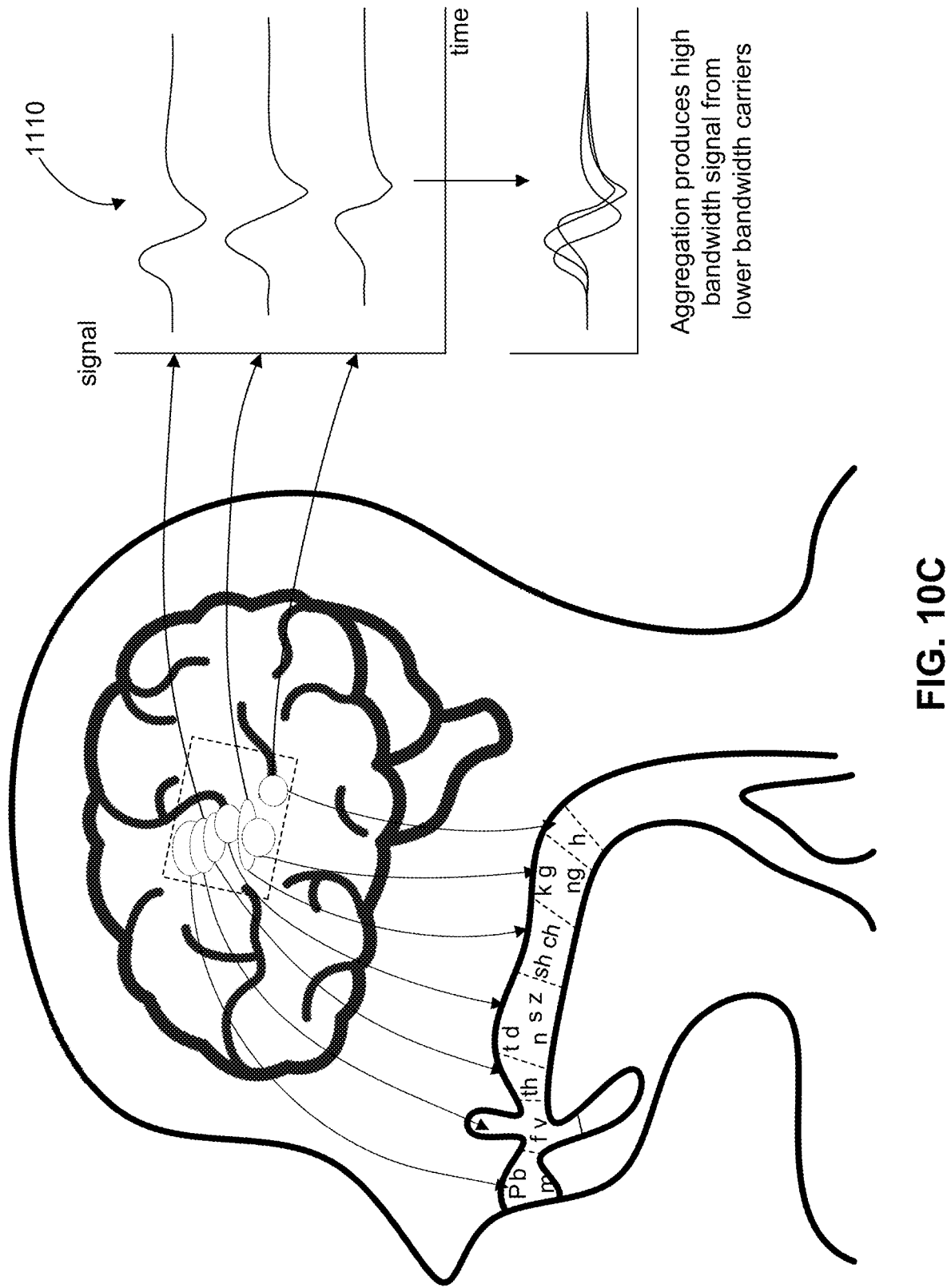
FIG. 10C illustrates a schematic of a neural data stream capturing information associated with different articulators, in relation to an embodiment of the method shown in FIG. 10A.

FIG. 10C depicts a schematic of a neural data stream capturing information associated with different articulators, in relation to an embodiment of the method shown in FIG. 10A. In the schematic shown in FIG. 10C, the neural data stream contains information from different brain/head regions that map to different articulators, where the different articulators are associated with different speech components (e.g., phonemes). In more detail, the neural data stream captures data associated with a first set of light signals corresponding to a first articulator, where the first articulator is a labial articulator associated with the phonemes "p", "b", and "m". The neural data stream also captures data associated with a second set of light signals corresponding to a second articulator, where the second articulator is a labiodental articulator associated with the phonemes "f" and "v". The neural data stream also captures data associated with a third set of light signals corresponding to a third articulator, where the third articulator is a dental articulator associated with the phoneme "th". The neural data stream also captures data associated with a fourth set of light signals corresponding to a fourth articulator, where the fourth articulator is an alveolar articulator associated with the phonemes "t", "d", "n", "s", and "z". The neural data stream also captures data associated with a fifth set of light signals corresponding to a fifth articulator, where the fifth articulator is a postalveolar articulator associated with the phonemes "sh" and "ch". The neural data stream also captures data associated with a sixth set of light signals corresponding to a sixth articulator, where the sixth articulator is a velar articulator associated with the phonemes "k", "g", and "ng". The neural data stream also captures data associated with a seventh set of light signals corresponding to a seventh articulator, where the seventh articulator is a glottal articulator associated with the phoneme "h". In alternative embodiments, however, the neural data stream can additionally or alternatively capture data associated with light signals corresponding to different articulators and/or different speech components. In relation to generation of the neural data stream, the detector array can be configured to separate detector subregions associated with different articulators, in order to increase distinction between signals associated with different articulators.

In relation to signals of the neural data stream shown in FIG. 10C, the signals associated with different articulators can be aggregated and processed, as described in downstream portions of the method 1000, in order to generate higher bandwidth signals from lower bandwidth carriers associated with articulator-specific signals received at different time points. As such, sequences of activation of different articulators associated with actual or imagined speech can generate low bandwidth carrier signals that can be processed, in relation to temporal and spatial factors, to produce a higher bandwidth signal that can be decoded.

In other embodiments, the system can generate a neural data stream using other techniques including any or more of: functional magnetic resonance imaging (fMRI), other forms of blood-oxygen-level dependent (BOLD) contrast imaging, near-infrared spectroscopy (NIRS), magnetoencephalography (MEG), electrocorticography (ECoG), electroencephalography (EEG), positron emission tomography, nuclear magnetic resonance (NMR) spectroscopy, single-photon emission computed tomography.

5.2 Method—Extracting Predicted User Action

Figure 10D:
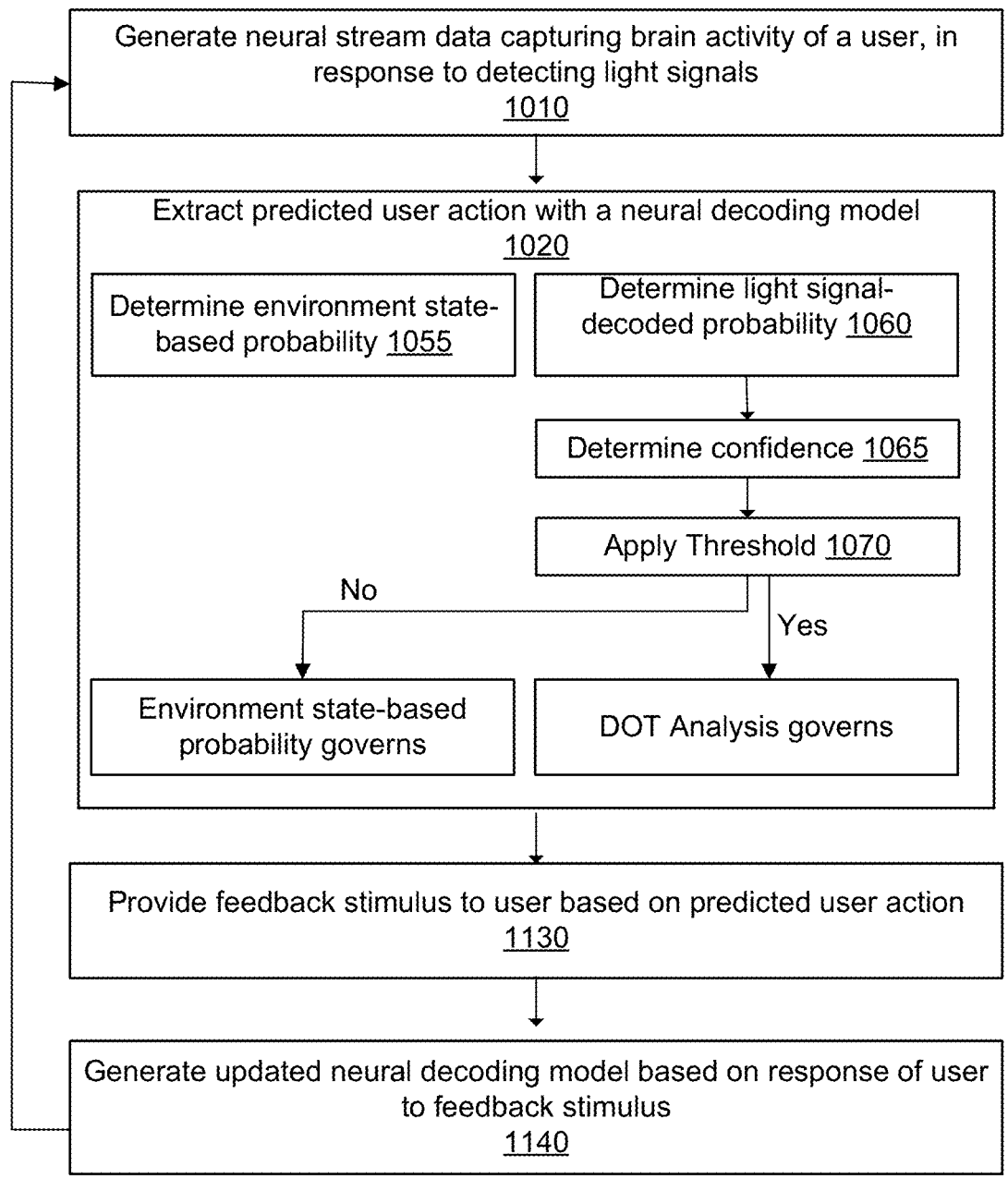
FIG. 10D illustrates a process flow of an embodiment of the method shown in FIG. 10A.

FIG. 10D depicts a flow chart of a portion of the method for neural decoding shown in FIG. 10A. As shown in FIG. 10D, the system (e.g., computing components) extracts 1020 a predicted user action upon processing the neural data stream with a neural decoding model, which functions to transform captured input signals associated with the neural data stream into decoded information that can be used to trigger responses (e.g., by environmental objects) that benefit the user in some manner. The predicted user action, as described above, can include a prediction of actual or imagined speech of the user, where the speech is associated with commands provided by the user to manipulate one or more objects in the environment of the user. The objects can be associated with a virtual or a real environment. For instance, the object can be a player or other entity in a virtual game environment, where the predicted user action is an action that manipulates behavior (e.g., movement) of the player or entity within the virtual game environment. In another example, the object can be a digital object associated with a virtual assistant, such that the predicted user action is an action that commands the virtual assistant to perform a task (e.g., in relation to scheduling, in relation to device operation state manipulation, in relation to executing communications with entities associated with the user, etc.). In another example, the object can be a connected object (e.g., a smart home light, smart home thermostat, smart home speaker, smart home appliance, other smart home device, etc.), such that the predicted user action is an action that affects operation of the connected object, through provision of control instructions to the connected object. In alternative embodiments, however, the predicted user action can be an action associated with different motor cortex functions (e.g., actual or imagined movement of another part of the body), different cognitive functions, different cognitive states (affective states, etc.). The action can, however, be another suitable action.

In relation to extracting predicted user actions, the BCI system (e.g., computing components of the system) can implement a neural decoding model that decodes the probability of a predicted action based upon environment/object state and an analysis of information from the neural data stream. As such, the system, as shown in FIG. 10D, can perform decoding by determining 1055 an empirical probability of an action due to state of the object and/or environment associated with the object, and by determining 1060 a light signal-decoded probability as determined from the neural data stream. In one embodiment, the probability function can be assumed to have the shape:

p(predicted user action|environment state, neural data) =softmax[$\alpha$*Q(predicted user action environment state)+ $\beta$*L(predicted user action neural data)], where p is the probability of the predicted user action. Q is determined from an analysis of probability of a given action from a set of candidate options based upon the environment or object state. L is a negative log-likelihood given by an estimator (e.g., neural network model) that is trained based upon incoming neural data from one or more users. The parameters $\alpha$ and $\beta$ are free hyperparameters.

In an example associated with a gaming environment, where the goal is to navigate a grid to drive a character toward a prize positioned within the grid, Q is determined by policy iteration over the available positions on the grid. In more detail, Q in this example is the negative of the distance from the position of the character to the position of the prize, where the distance can be measured by Dijkstra's algorithm or another distance-determining algorithm. In different environments (e.g., other virtual or real environments) with different objects, however, Q can be used to determine a probability of an action based on environment state with another process.

In an example where the predicted user action is associated with actual or imagined speech commands, the neural decoding model can determine L upon receiving and aggregating sequences of signals associated with the speech articulators, in order to form single or multi-consonant words that represent different commands. As such, the neural decoding model can transform the neural data stream into a set of speech components mapped to a set of motor cortex articulators associated with the head region or, can transform a sequence of activated motor cortex articulators, captured in the set of light signals of the neural data stream, into one or more phoneme chains representative of the commands. Based on the set of articulators from which signals are able to be captured by the detector array, the phoneme chains can be literally translated into the commands (e.g., phoneme chains that form directional words). Additionally or alternatively, the phoneme chains can be trained representations of a spoken version of the commands. For instance, a phoneme chain of "h" "th" "m" detected in the neural data stream can translate to "hotham", a phoneme chain of "v" "d" "k" detected in the neural data stream can translate to "vadok", a phoneme chain of "p" "ch" "th" detected in the neural data stream can translate to "poochoth", and a phoneme chain of "k" "v" "n" detected in the neural data stream can translate to "kevin", where the representative words "hotham", "vadok", "poochoth", and "kevin" map to different commands (e.g., commands that move a character in different directions, such as left, right, up, and down, in a virtual environment).

Also shown in FIG. 10D, implementation of the neural decoding model can include modulating which components (e.g., an environment state-based component, a neural data stream-based component) govern the output of the model. In more detail, as shown in FIG. 14C, the controller can determine 1055 an environment state-based probability associated with the predicted user action and determine 1060 a light signal-decoded probability associated with the user action. The controller can also determine 1065 a value of a confidence parameter associated with the light signal-decoded probability, and compare 1070 the value of the confidence parameter to a threshold condition. Then, if the threshold condition is satisfied, the output of the neural decoding model can be based upon the light signal-decoded data (e.g., as determined using a diffuse optical tomography analysis). However, if the threshold condition is not satisfied, the output of the neural decoding model can be based upon the environment state-based probability analysis. Alternatively, the controller can implement a weighting function that weighs the confidences in each of the environment state-based analyses and the light-signal decoded analyses, and provides an output that combines the weighted probability components as an aggregated output (e.g., based on convex combination, based on another combination algorithm).

As such, without knowledge by the user, the controller can ensure that the neural decoding model 1020 outputs a predicted user action, even if the confidence in the analysis of the action captured in the neural data stream is low, by using an empirical probability determined from the environment state. Furthermore, the controller can implement training data from situations where the predicted user action is known, in order to increase the accuracy of the light-decoded probabilities. Then, as the confidence in the light signal-decoded probability based on analysis of the neural data stream increases, the controller can primarily output predicted user actions based on analysis of the neural data stream, as the accuracy in decoding light signals of the neural data stream increases.

Figure 10E:
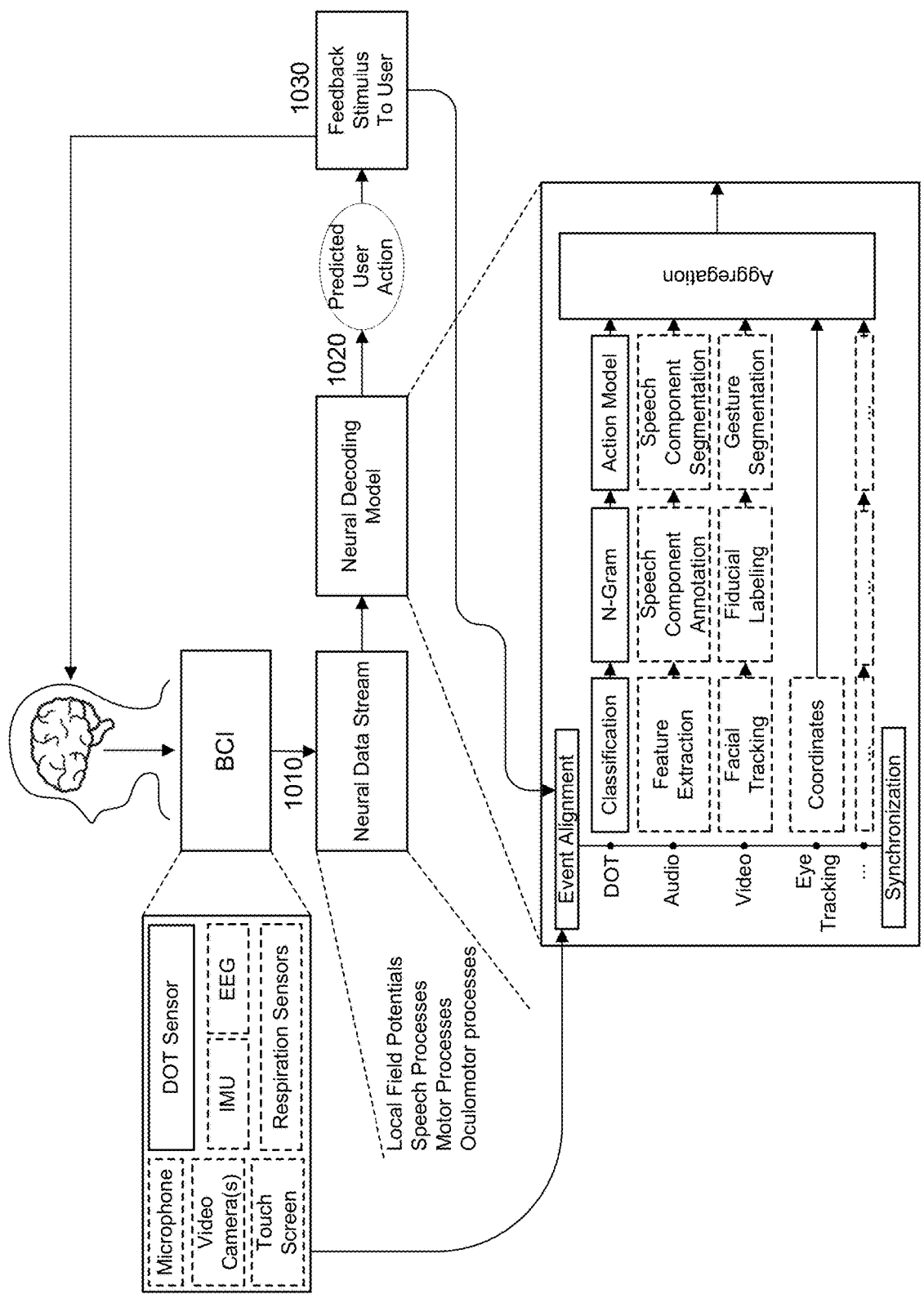
FIG. 10E illustrates an expanded view of a portion of the process flow shown in FIG. 10D.

FIG. 10E depicts an expanded view of a portion of the process flow shown in FIG. 10D, in relation to implementation of the neural decoding model as applied to input signals derived from sensors associated with the brain computer interface. As shown, input signals can be associated with hemodynamic responses captured in light signals. Input signals can additionally or alternatively include local field potentials, signals capturing speech processes (actual or imagined speech processes), signals capturing oculomotor processes, signals capturing other motor processes, other biometric data (e.g., associated with respiration, etc.) and other suitable input signals, based on sensor outputs of the BCI. In particular, an embodiment of the detector array can generate light signals associated with hemodynamic response in relation to different articulators, as described above. Additionally, one or more microphones can generate audio signals (e.g., capturing speech information) that can supplement data used to generate the predicted user action. Additionally, one or more video cameras can generate video data associated with the user's face or eyes and/or an environment of the user that can supplement data used to generate the predicted user action. Additionally, one or more touch sensors can generate signals indicative of motor skill activities of the user that can supplement data used to generate the predicted user action. Additionally, one or more motion sensors (e.g., of an inertial measurement unit) can generate signals indicative of motion of the user that can supplement data used to generate the predicted user action. Additionally, other brain activity sensors (e.g., electrodes for electroencephalography, etc.) can generate signals from electrical potentials that can supplement data used to generate the predicted user action. Additionally, other biometric sensors (e.g., respiration sensors, cardiovascular parameter sensors, etc.) can generate signals that can supplement data used to generate the predicted user action.

In relation to processing of the neural data stream, input light signals derived from one or more embodiments of the detector array described above can be classified by the controller hosting the neural decoding model into groups associated with different articulators (e.g., different articulators associated with different speech components, an example of which is shown in FIG. 14C). Then, outputs of the classification can be assembled (e.g., into n-grams), based upon temporal factors or other factors. The controller hosting the neural decoding model can then process the assembled information with an action prediction model. In one embodiment, the controller can transform signals associated with a sequence of activated motor cortex articulators (e.g., as captured in a set of light signals) into a phoneme chain representative of a command intended to be executed by the user.

If including analysis of audio signals in the neural decoding model, the controller hosting the neural decoding model can also extract features of the audio signals, determine and annotate speech components or other audio components from the audio signals, and perform a segmentation operation to determine boundaries between individual speech components, in relation to a user action. If including analysis of video signals in the neural decoding model, the controller hosting the neural decoding model can also implement facial feature tracking algorithms, with fiducial labeling and gesture segmentation models, in relation to detecting a user action. The controller can additionally or alternatively process video signals in order to track motions of the eye(s) of the user, in order to determine coordinates of objects that the user is looking at and/or dwell time, in relation to a user action. The neural decoding model can additionally or alternatively accept other input signals, which can be aggregated by architecture of the neural decoding model to combine features into an output of a predicted user action (e.g., with a confidence score).

In relation to the neural decoding model, the controller can include architecture for synchronization of input signals associated with the same or different sensors, in relation to an event (e.g., an environment state, an object state, a stimulus, a feedback stimulus provided based on a predicted user action, as described in more detail below, etc.). In order to synchronize input signals, the controller can include architecture for signal registration (e.g., based upon temporal signatures within different signals, based upon interpolation of signals with different associated sampling rates, etc.), to a desired degree (e.g., with millisecond alignment, with microsecond alignment, etc.). As such, the controller implements the neural decoding model to extract predicted user actions contemporaneously (e.g., within a time threshold to) a time point associated with an event, such as a state of an environment or object associated with the user.

5.3 Method—Providing Feedback Stimulus

Figure 10F:
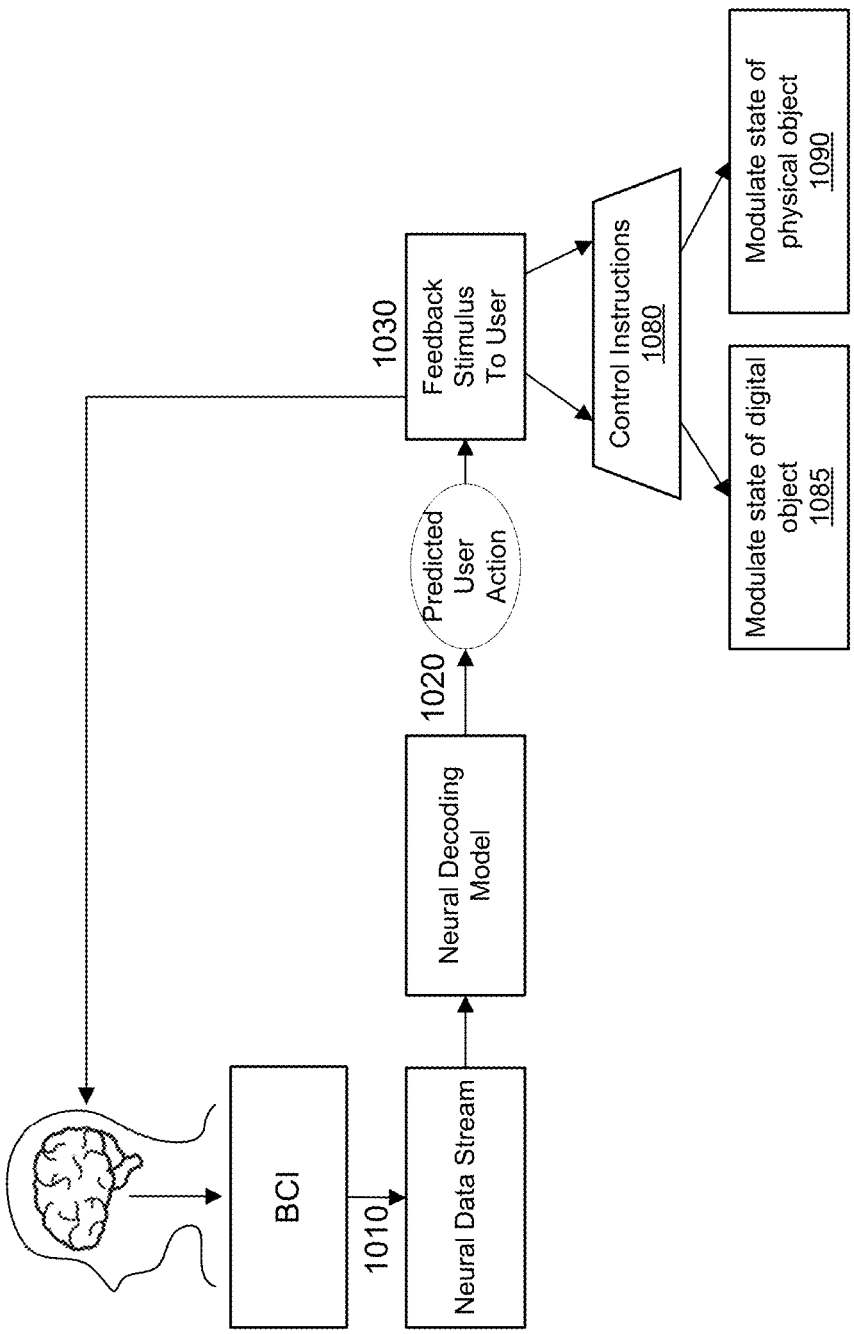
FIG. 10F illustrates an expanded view of a portion of the process flow shown in FIG. 10D.

As shown in FIGS. 10A, 10D, and 10F, where FIG. 10F illustrates an expanded view of a portion of the process flow shown in FIG. 10B, the controller provides 1030 a feedback stimulus to the user based on the predicted user action output by the neural decoding model. The feedback stimulus can be a representation of the predicted user action output by the neural decoding model, in text or other visual format, in audio format, and/or in haptic format. For instance, if the predicted user action is associated with a command (e.g., a command to manipulate an object) or request, the feedback stimulus can be a textual representation of the command or request, or a symbolic representation of the command or request. In a specific example, if the command is an indication by the user that the user wants to move an object in a direction, the feedback stimulus can be a rendered text description of the direction or a rendered arrow depicting the direction, where the controller generates instructions for rendering the feedback stimulus at a display. In another specific example, if the command is an indication by the user that the user wants to move an object in a direction, the feedback stimulus can be an audio output that states the direction in speech, where the controller generates instructions for transmitting audio through a speaker of a device associated with the user. The representation of the command, provided to the user as the feedback stimulus, can be validated by the user (e.g., the user can indicate that the predicted user action is correct, based upon the feedback stimulus), as a transitional step to execution of the command or request by the controller or other device. Additionally, as described below, the representation of the command, provided to the user as the feedback stimulus, can be used in a co-learning process in order to train the user's behavior (e.g., to provide feedback to the user so that the user can tune his/her behaviors to provide signals that are more easily decoded), such that training of the neural decoding model occurs in coordination with training of user behaviors to increase the accuracy of the neural decoding model.

In providing the feedback stimulus, the controller can also generate instructions for execution of a command or request by the user, in relation to modulation of a state of a digital object 1085 or a physical object 1090, with generation 1080 of control instructions in a computer-readable medium for object modulation, several examples of which are described below.

In the context of a game architected in a digital platform, the feedback stimulus can include direct manipulation of a user's character in the game, in terms of motion, behavior, or another action performable by the user's character. In a specific example, execution of the command can include moving the user's character in the game environment, in direct response to the predicted user action being associated with a direction in which the user intends the character to move. In the context of a game architected in a digital platform, the feedback stimulus can include direct manipulation of a game environment, in terms of adjustable parameters in the virtual environment.

In the context of a virtual assistant platform, the feedback stimulus can include generation of control instructions for the virtual assistant to navigate and/or manipulate systems in order to perform a task for the user. For instance, the controller can generate control instructions that instruct the virtual assistant to execute communication (e.g., in a text message, in an audio message, etc.) with an entity associated with the user, to generate a reminder, to perform a calendar-related task, or to perform another task.

In the context of a virtual environment, with menus or other selectable objects, the feedback stimulus can include execution of instructions for selection of the object or navigation of a menu, based upon the predicted user action.

In the context of connected devices physically associated with a real environment of the user, the feedback stimulus can include manipulation of operation states of the connected device(s). In examples, the connected device(s) can include one or more of: temperature control devices, light control devices, speakers, locks, appliances, and other connected devices. In providing the feedback stimulus, the controller can generate control instructions for adjusting operational states of devices (e.g., turn off device, turn on device, transition device to idle, adjust device brightness, adjust device output color, adjust device output volume, adjust device sound output profile, adjust microphone operation state, adjust temperature output, adjust lock state, adjust appliance operation state, etc.)

In other contexts, the feedback stimulus may not be related to a command or request. For instance, the predicted user action can be a subconscious cognitive state or affective state, and the controller can generate and/or execute instructions for manipulation of an object or environment based upon the subconscious cognitive state or affective state.

5.4 Method—Co-Learning

As shown in FIGS. 10A and 10B and described above, the system also implements one or more co-learning processes 1040, 1050 for improvement of the neural decoding model and/or behavior of the user. In relation to the co-learning processes, the controller implementing the method 1400 provides a closed loop process whereby the neural decoding model is updated and trained as the user interacts with content or other stimuli, and provides additional light-derived signals that capture brain activity. Additionally, the feedback stimuli provided to the user produces a behavior by the user and can be used to train the user in relation to adjusting responses to the environment in a manner that is more efficiently decoded by the neural decoding model. As such, the method 1400 can implement computing architecture that inputs an output derived from the feedback stimulus (e.g., verification that the feedback stimulus was appropriate in relation to a user action) back into the neural decoding model, in order to refine the neural decoding model. In relation to a closed-loop system, the controller can, based upon a behavior of the user in response to the feedback stimulus, process additional signals from the user to generate additional predicted user actions (with refinement of the neural decoding model). Then, based upon the additional predicted user actions, the controller can provide additional feedback stimuli to the user, derivatives of which and/or responses to which can be used to further refine the neural decoding model.

6. CONCLUSION

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a nontransitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A flexible printed circuit assembly (FPCA) of a brain-computer interface (BCI) module, the FPCA configured to interconnect a plurality of emitter assemblies and a plurality of detector assemblies of the BCI module and comprising:
    a connector portion for connecting the FPCA to a controller of the BCI module;
    a plurality of rigid sections, each rigid section of a first subset of rigid sections configured to mount an emitter assembly from the plurality of emitter assemblies, and each rigid section of a second subset of rigid sections configured to mount a detector assembly from the plurality of detector assemblies; and
    a plurality of flexible sections, each flexible section coupled to two or more rigid sections, wherein each flexible section of the plurality sections is configured to attach to one or more rigid sections of the plurality of rigid sections to each other, the plurality of flexible sections comprising a plurality of traces for routing electrical signals from the connector portion to each of the rigid sections,
    wherein each rigid section is configured to mount a ferrule of an array of ferrules and the flexible sections coupled to the rigid section bend to position the mounted ferrule independently of other ferrules of the array of ferrules.

2. The FPCA of claim 1, wherein the FPCA is configured to stretch to allow the BCI module to conform to a head of a user.

3. The FPCA of claim 1, wherein the FPCA is configured to mount an array of ferrules such that each ferrule of the array comprises an independent controller circuitry, each independent controller circuitry configured to operate an optical element enclosed in a corresponding ferrule of the array of ferrules.

4. The FPCA of claim 1, wherein the FPCA is configured to mount emitter and detector assemblies in a hexagonal formation.

5. The FPCA of claim 4, wherein each rigid section of a subset of rigid sections is attached to three rigid sections of the plurality of rigid sections by corresponding flexible sections of the plurality of flexible sections.

6. The FPCA of claim 1, wherein each rigid section of the plurality of rigid sections is attached to six other rigid sections of the plurality through six corresponding flexible sections of the plurality of flexible sections.

7. The FPCA of claim 1, wherein each detector assembly mounted to the FPCA is surrounded by one or more of the emitter assemblies mounted to the FPCA.

8. A brain-computer interface (BCI) module for enabling a user to interface a computing device, the BCI module comprising:
    a flexible printed circuit assembly (FPCA) of the BCI module, the FPCA configured to interconnect a plurality of emitter assemblies and a plurality of detector assemblies of the BCI module and comprising:
        a connector portion for connecting the FPCA to a controller of the BCI module;

a plurality of rigid sections, each rigid section of a first subset of rigid sections configured to mount an emitter assembly from the plurality of emitter assemblies, and each rigid section of a second subset of rigid sections configured to mount a detector assembly from the plurality of detector assemblies, each rigid section configured to dispose a ferrule of an array of ferrules on a surface of the rigid section; and a plurality of flexible sections, each flexible section coupled to two or more rigid sections, wherein each flexible section of the plurality sections is configured to attach to one or more rigid sections of the plurality of rigid sections to each other, the plurality of flexible sections comprising a plurality of traces for routing electrical signals from the connector portion to each of the rigid sections;

wherein each rigid section is configured to mount a ferrule of an array of ferrules and the flexible sections coupled to the rigid section bend to position the mounted ferrule independently of other ferrules of the array of ferrules.

9. The BCI module of claim 8, wherein the FPCA is configured to stretch to allow the BCI module to conform to a head of a user.

10. The BCI module of claim 8, wherein the FPCA is configured to mount an array of ferrules such that each ferrule of the array comprises an independent controller circuitry, each independent controller circuitry configured to operate an optical element enclosed in a corresponding ferrule of the array of ferrules.

11. The BCI module of claim 8, wherein the FPCA is configured to mount emitter and detector assemblies in a hexagonal formation.

12. The BCI module of claim 11, wherein each rigid section of a subset of rigid sections is attached to three rigid sections of the plurality of rigid sections by corresponding flexible sections of the plurality of flexible sections.

13. The BCI module of claim 8, wherein each rigid section of the plurality of rigid sections is attached to six other rigid sections of the plurality through six corresponding flexible sections of the plurality of flexible sections.

14. The BCI module of claim 8, wherein each detector assembly mounted to the FPCA is surrounded by one or more of the emitter assemblies mounted to the FPCA.

* * * * *